US006590127B1

(12) United States Patent
Sinha et al.

(10) Patent No.: US 6,590,127 B1
(45) Date of Patent: Jul. 8, 2003

(54) PROCESS FOR THE PREPARATION OF PHARMACOLOGICALLY ACTIVE α-ASARONE FROM TOXIC β-ASARONE RICH *ACORUS CALAMUS* OIL

(75) Inventors: Arun Kumar Sinha, Himachal Pradesh (IN); Bhupendra Prasad Joshi, Himachal Pradesh (IN); Ruchi Acharya, Himachal Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/107,844

(22) Filed: Mar. 28, 2002

(51) Int. Cl.$^7$ .......................... C07C 45/00; C07C 47/56; C07C 41/00; C07C 27/00

(52) U.S. Cl. ...................... 568/315; 568/322; 568/426; 568/442; 568/627; 568/630; 568/648; 568/654; 568/814

(58) Field of Search ................................ 568/315, 322, 568/426, 442, 627, 630, 648, 654, 814

(56) References Cited

U.S. PATENT DOCUMENTS 2,529,186 A  * 11/1950 Richmond
3,028,419 A  *  4/1962 Bloch
3,852,305 A  * 12/1974 Nagase et al.

OTHER PUBLICATIONS

Devaan et al. "Isolation of 2,4,5–trimethoxylallylbenzene From *Caesulia Axillaries* Oil". Aust. J. Chem., 1968, (21) 3001–3.*
Abel, G., "Chomosomenschädigende Wirkung von β–Asaron in menschlichen Lymphocyten," *Planta Med.* pp. 251–253 (1987).
Belanger, A. et al., "Essential oil composition of *Acorus calamus* from Quebec," Chemical Abstract No. 127:362513, 1999 American Chemical Society.
Bonaccorsi, I. et al., "Studies on essential oil–bearing plants of Bangladesh. Part VII. Composition of the rhizomes oil of *Acorus calamus L.* (sweet flag)," Chemical Abstract No. 128:286182, 1999 American Chemical Society.
Bucher, M. et al., "Glycolytic gene expression in amphibious *Acorus calamus L.* under natural conditions," Chemical Abstract No. 124:97884, 1999 American Chemical Society.
Chamorro, G. et al., "Hypolipidemic activity of dimethoxy unconjugated propenyl side–chain α–asarone in mice," Chemical Abstract No. 129:103752, 1999 American Chemical Society.
Choudary, B.M. et al., "Hydrotalcite–like compounds for liquid–phase oxidation of benzylic hydrocarbons," *Indian Journal of Chemistry* 36B:278–280 (Mar. 1997).
Crawford, R. et al., "Oxygen deprivation stress in a changing environment," Chemical Abstract No. 124–226435, 1999 American Chemical Society.

Curró, P. et al., "Determination of –asarone, safrole, isosafrole and anethole in alcoholic drinks by high–performance liquid chromatography," *Journal of Chromatography A,* 404:273–278 (Abstract only) (1987) Elsevier Science B.V.
Cutler, H., "Natural product flavor compounds as potential antimicrobials, insecticides and medicinals," Chemical Abstract No. 124:79295, 1999 American Chemical Society.
Deters, M. et al., "Influence of Curcumin on Cyclosporin–Induced Reduction of Biliary Bilirubin and Cholesterol Excretion and on Biliary Excretion of Cyclosporin and it Metabolites," *Planta Med.* 66:429–434 (2000) Georg Thieme Verlag Stuttgart, New York, USA.
Ding, L. et al., "Determination of α–Asarone in *Acorus tatarinowii Schott,* and its essential oil by GC," Chemical Abstract No. 125:323006, 1999 American Chemical Society.
Dung, N. et al., "Volatile Constituents of the Aerial Parts of *Orthodon calveriei Level.* from Vietnam," *J. Essent. Oil Res.* 7:111–112 (Jan./Feb. 1995) Allured Publishing Corp.
Enqiquez, R.G. et al., "Propenylbenzenes from *Guatteria Gaumeri,*" *Phytochemistry* 19:2024–2025 (1980) Pergamon Press Ltd., England.
Freyer, R. et al., "Occurrence of plastid RNA editing in all major lineages of land plants," Chemical Abstract No. 127:133301, 1999 American Chemical Society.
Fukuyama, Y. et al., "Bicycloillicinone asarone acetal. A novel prenylated $C_6$—$C_3$ compound increasing choline acetyltransferase (ChAT) activity from *Illicium tashiroi,*" Chemical Abstract No. 127:181002.
Garduno, L. et al., "Hypolipidaemic activity of α–asarone in mice," *Journal of Ethnopharmacology* 55:161–163 (1997) Elsevier Science Ireland Ltd.
Garduno, L. et al., "Hypolipidemic activity of α–asarone in mice," Chemical Abstract No. 126:113020, 1999 American Chemical Society.
Gonzalez, M. et al., "Prenylated benzopyran derivatives from two Polyalthia species," Chemical Abstract No. 126:57453, 1999 American Chemical Society.
Gora, J. et al., "Chemical composition of some Polish commercial essential oils," Chemical Abstract No. 128:16268, 1999 American Chemical Society.

(List continued on next page.)

Primary Examiner—Johann Richter
Assistant Examiner—Sikarl A. Witherspoon
(74) Attorney, Agent, or Firm—Foley & Lardner

(57) ABSTRACT

The present invention relates to a process for the preparation of high purity and yield α-asarone, trans 2,4,5-trimethoxy cinnamaldehyde, 2,4,5-trimethoxy-phenyl propionone, from β-asarone or β-asarone rich *Acorus calamus* oil containing α and γ-asarone by hydrogenating, followed by treatment with DDQ with or without solid support of silica gel or alumina in dry organic solvent and α-asarone can also be obtained by treating the hydrogenated product of β-asarone or β-asarone rich *Acorus calamus* with DDQ in an aqueous organic solvent to obtain an intermediate 2,4,5-trimethoxy phenyl propionone, which in turn is reduced with sodium-borohydride to obtain the corresponding 2,4,5-trimethoxy-phenyl propanol and followed by final treatment with a dehydrating agent.

22 Claims, 8 Drawing Sheets

OTHER PUBLICATIONS

Hara, T. et al., "Resin composition for photomagnetic recording material protective coating, the recording material with the coating, and coating method," Chemical Abstract No. 124:216238, 1999 American Chemical Society.

Hernández, A. et al., "Inhibition of Lipid Synthesis and Secretion in Long–Term Cultures of Adult Rat Hepatocytes by α–Asarone," *Planta Med.* 59:121–124 (1993).

Högberg, T. et al., "Potential Antipsychotic Agents. 5. Synthesis and Antidopaminergic Properties of Substituted 5,6–Dimethoxysalicylamides and Related Compounds," *J. Med. Chem.* 33:1155–1163 (1990) American Chemical Society.

Horie, T. et al., "Syntheses of 5,7,8–and 5,6,7–Trioxygenated 3–Alkyl–3', 4'–dihydroxyflavones and Their Inhibitory Activities against Arachidonate 5–Lipoxygenase," *J. Med. Chem.* 34(7):2169–2176 (1991).

Horste, B. et al., "Composition for cleaning of facial skin," Chemical Abstract No. 126:108644, 1999 American Chemical Society.

Hu, J. et al., "Phenylpropanes from *Acorus tatarinowii*," *Planta Med.* 66:662–664 (2000) Georg Thieme Verlag Stuttgart, New York, USA.

Idaka, E., "Soil activator containing deep–sea brines," Chemical Abstract No. 129:81225, 1999 American Chemical Society.

Ikeda, S. et al., "Preparation of indolypropenone derivatives as antitumor agents," Chemical Abstract No. 126:47095, 1999 American Chemical Society.

Jaimol, T. et al., "Selective propionylation of veratrole to 3,4–dimethoxypropiophenone using zeolite H–beta catalysts," *Applied Catalysis A General* 214:1–10 (2001) Elsevier Science Ltd.

Kato, H. et al., "Molecular systematics of the *Trilliaceae sensu lato* as inferred from rbcL sequence data," Chemical Abstract No. 124:5065, 1999 American Chemical Society.

Keller, K. et al., "Spasmolytische Wirkung des *Isoasaronfreien Kalmus*," *Planta Med.*, pp. 6–9 (1985).

Kikuzaki, H. et al., "Phenylbutanoid dimers from the leaves of *Alpinia flabellata*," *Phytochemistry* 56:109–114 (2001) Elsevier Science Ltd.

Kim, S.G. et al., "New studies on trans–anethole oxide and trans–asarone oxide," *Carcinogenesis*, 20(7):1303–1307 (Abstract only), Elsevier Science B.V.

Kozub, D. et al., "Nitrogen removal in constructed wetlands treating high nitrogen landfill leachate.," Chemical Abstract No. 129:334922, 1999 American Chemical Society.

Kreuter, M. et al., "Process for removing unwanted lipophilic impurity or residue from drinks or vegetable preparations," Chemical Abstract No. 125:246102, 1999 American Chemical Society.

Lazutka, J.R. et al., "Genotoxicity of dill (*Anethum graveolens* L.), peppermint (*Menthaxpiperita* L.) and pine (*Pinue sylvestris* L.) essential oils in human lymphocytes and *Drosophila melanogaster*," *Food and Chemical Toxicology* 39:485–492 (2001) Elsevier Science Ltd.

López, M. et al., "α–Asarone Toxicity in Long–Term Cultures of Adult Rat Hepatocytes," *Planta Med.* 59:115–120 (1993).

Makarov, N. et al., "Tonic formulation," Chemical Abstract No. 128:53223, 1999 American Chemical Society.

Masuda, T. et al., "Synthesis of (±) Cassumunins A and B. New Circuminoid Antioxidants Having Protective Activity of the Living Cell Against Oxidative Damage," Chemical Abstract No. 128:308339; 1999 American Chemical Society.

Mazza, Giacomo, "Gas chromatographic and mass spectrometric studies of the constituents of the rhizome of calamus. I. The volatile constituents of the essential oil," *Journal of Chromatography A* 328:179–194 (Abstract only) (1985) Elsevier Science B.V.

Mazza, Giacomo, "Gas chromatographic and mass spectrometric studies of the constituents of the rhizome of calamus. II. The volatile constituents of alcoholic extracts," *Journal of Chromatography A* 328:195–206 (Abstract only) (1995) Elsevier Science B.V.

Mihara, T. et al., "Compositions containing asarones extracted from plants for prevention and improvement of vision disorders," Chemical Abstract No. 130:57186, 1999 American Chemical Society.

Motley, T., "The Enthnobotany of Sweet Flag, *Acorus Calamus* (Araceae)," *Economic Botany* 48(4):397–412 (1994) The New York Botanical Garden, Bronx, New York, USA.

Nadot, S. et al., "A phylogenetic analysis of monocotyledons based on the chloroplast gene rps4, using parsimony and a new numerical phenetics method," Chemical Abstract No. 124:46862, 1999 American Chemical Society.

Nakakita, H. et al., "A new bioassay detecting for IGR activity with larvae of *Tribolium freemani Hinton* (Coleoptera: Tenebrionidae)," Chemical Abstract No. 125:3554, 1999 American Chemical Society.

Narayana, D.B.A. et al., "Quantitative detection of β–asarone in *Acorus calamus* using HPTLC," Chemical Abstract No. 124:97884, 1999 American Chemical Society.

Nawamaki, K. et al., "Sesquiterpenoids from *Acorus calamus* as germination inhibitors," Chemical Abstract No. 126:57449, 1999 American Chemical Society.

Nawamaki, K. et al., "Sesquiterpenoids from *Acorus calamus* as germination inhibitors," Chemical Abstract No. 126:57443, 1999 American Chemical Society.

Nigam, M.C. et al., "GC–MS Examination of Essential Oil of *Acorus Calamus*," *Indian Perfumer* 34(4):282–285 (1990).

Nishizawa, Y. et al., "Hair growth stimulants containing plant extracts and other agents for synergistic effects," Chemical Abstract No. 124:324998, 1999 American Chemical Society.

Ohtsubo, H. et al., "Diagnostical investigation of Acori rhizomes. (2). Histological and chemical _of Acori rhizomes in Asian markets," Chemical Abstract No. 128:323_, 1999 American Chemical Society.

Oprean, R. et al., "Comparison of GC–MS and TLC techniques for asarone isomers determination," *Journal of Pharmaceutical and Biomedical Analysis* 18:227–234 (1998) Elsevier Science B.V.

Oprean, R. et al., "Comparison of GC–MS and TLC techniques for asarone isomers determination," Chemical Abstract No. 130:29297, 1999 American Chemical Society.

Oprean, R. et al., "Essential oils analysis. I. Evaluation of essential oils composition using both GC and MS fingerprints," *Journal of Pharmaceutical and Biomedical Analysis* 18:651–657 (1998) Elsevier Science B.V.

OTHER PUBLICATIONS

Oprean, R. et al., "Essential oils analysis. II. Mass spectra identification of terpene and phenylpropane derivatives," *Journal of Pharmaceutical and Biomedical Analysis* 24:1163–1168 (2001) Elsevier Science B.V.

Parmar, V. et al., "Phytochemistry of the Genus Piper," *Phytochemistry* 46(4):597–599 and 616–627 (1997) Elsevier Science Ltd., Great Britain.

Patra, A. et al., "Constituents of *Acorus calamus Linn.*," pp. 412–414.

Petrov, K.A. et al., "The effect of esential oils of *Ledum palustre L., Acorus calamus L.,* and *Artemisia jacutica Drob.* on the biotests growth," Chemical Abstract No. 129:173064, 1999 American Chemical Society.

Poplawski, J. et al., "Synthesis and Hypolipidemic and Antiplatelet Activities of a α–Asarone Isomers in Human (in Vitro), Mice (in Vivo), and Rats (In Vivo)," *J. Med. Chem.* 43:3671–3676 (2000) American Chemical Society.

Rai, R. et al., "Triterpenoid saponins from *Acorus calamus,*" Chemical Abstract No. 129:186688, 1999 American Chemical Society.

Roslyakova, T. et al., "Tone lacquer for hair," Chemical Abstract No. 126:50846, 1999 American Chemical Society Saller, R. et al., "Bach flowers. No therapy substitute," Chemical Abstract No. 124:211694, 1999 American Chemical Society.

Samudralwar, D. et al., "Minor and trace elemental determination in the Indian herbal and other medicinal preparations," Chemical Abstract No. 125:256917, 1999 American Chemical Society.

Sargunas, G. et al., "Formulation for alcoholic bitters," Chemical Abstract No. 127:4412, 1999 American Chemical Society.

Saxena, D., "Phenyl Indane From *Acorus Calamus,*" *Phytochemistry* 25(2):553–555 (1986) Pergamon Press Ltd., Great Britain.

Schiestl, R.H. et al., "Safrole, eugenol and methyleugenol induce intrachromosomal recombination in yeast," *Mutation Research* 224(4):427–436 (Abstract only) Dec. 1989, ISSN: 0027–5107.

Sedova, I. et al., "Depilatory formulations," Chemical Abstract No. 127:195264, 1999 American Chemical Society.

Sharma, P.K. et al., "Synthesis and Some Pharmacological Actions of Asarone," *J. Appl. Chem.* 32(4):236–238 (1969).

Shen, R. et al., "6–Hydroxycatecholine, a choline–mimicking analog of the selective neurotoxin, 6–hydroxydopamine," Chemical Abstract No. 126:2707, 1999 American Chemical Society.

Spilkova, J. et al., "Determination of β–asarone in the plant drug *Radix calami* by means of gas chromatography," Chemical Abstract No. 125:123981, 1999 American Chemical Society.

Srivastava, M. et al., "Rhizome oil of *Acorus calamus Linn.* Characterization by GC–MS and study of its bioefficacy against pulse beetle *Callasobruchus chinesis Linn.*," Chemical Abstract No. 127:159004, 1999 American Chemical Society.

Stauffer, S. et al., "Pyrazole Ligands: Structure–Affinity/Activity Relationships and Estrogen Receptor–α–Selective Agonists," *J. Med. Chem.* 43:4934–4947 (2000) American Chemical Society.

Sugimoto, N. et al., "Pharmacognostical investigation of Acori rhizomes. (2). Histological and chemical studies of Acorn rhizomes in Asia Markets," Chemical Abstract No. 128:32372, 1999 American Chemical Society.

Sugimoto, N. et al., "Pharmacognostical investigations of Acori rhizomes. (1). Histological and chemical studies of rhizomes of *A. calamus* and *A. gramineus* distributed in Japan," Chemical Abstract No. 127:245482, 1999 American Chemical Society.

Suri, O.P. et al., "Synthesis of Apocynin, a Choleretic Constituent of *Picrorhiza kurroa* & Its Homologues," *Indian Journal of Chemistry,* 26B:587–588 Jun. 1987.

Tamas, M. et al., "Identification and quantitative determination of β–asarone in the essential oil of *Acorus calamus L.*," Chemical Abstract No. 126:161965, 1999 American Chemical Society.

Tanaka, N. et al., "Bubble bath compositions containing surfactants and plant extracts," Chemical Abstract No. 126:203589, 1999 American Chemical Society.

Tarhanen, J. et al., "_Emission Composition of Essential Oil in Two Carrot Varieties," Chemical Abstract No. 129:20_ 6985, 1999 American Chemical Society.

Viviana de Oliveira Santos, B. et al., "2,4,5–Trimethoxypropiophenone from *Piper marginatum,*" *Biochemical systematics and Ecology* 27:539–541 (1999) Elsevier Science Ltd.

Wang, M. et al., "Two new amides from the roots of *Acorus tatarinowii Schott,*" Chemical Abstract No. 126:199389, 1999 American Chemical Society.

Wang, M. et al., "Two new isopimarane dieterpenes from the roots of *Acorus tatarinowii Schott,*" Chemical Abstract No. 126:212269, 1999 American Chemical Society.

Wang, Q. et al., "Determination of the relevant constituents in *Rensenzaizao Wan* and *Dahuoluo Dan,*" Chemical Abstract No. 125:204632, 1999 American Chemical Society.

Wang, Y. et al., "Long–term performance of two constructed wetlands for the treatment of domestic wastewater," Chemical Abstract No. _:_34917, 1999 American Chemical Society.

Wu, C. et al., "Advances in studies of α–asarone," Chemical Abstract No. 128:10025, 1999 American Chemical Society.

Wu, L. et al., "NMR studies on the stereostructure of calamenone," Chemical Abstract No. 129:203108, 1999 American Chemical Society.

Yang, Z. et al., "Absolute bioavailability of synthetic asarone in healthy volunteers," Chemical Abstract No. 128:79883, 1999 American Chemical Society.

Zanoli, P. et al., "Sedative and hypothermic effects induced by β–asarone, a main component in *Acorus calamus,*" Chemical Abstract No. 130:60958, 1999 American Chemical Society.

Zava, D. et al., "Estrogen and progestin bioactivity of foods, herbs and spices," Chemical Abstract No. 128:243162, 1999 American Chemical Society.

\* cited by examiner $^1$H NMR (300 MHz) spectra of α-asarone in CDCl$_3$ $^{13}$C NMR (75.4 MHz) spectra of α–asarone in CDCl$_3$ $^1$H NMR (300 MHz) spectra of trans-2,4,5-trimethoxycinnamaldehyde in CDCl$_3$ $^1$H NMR (300 MHz) spectra of 1-(2,4,5-trimethoxy)phenyl-1-propanone in CDCl$_3$ $^{13}$C NMR (75.4 MHz) spectra of 1-(2,4,5-trimethoxy)phenyl-1-propanone in CDCl$_3$ $^{13}$C NMR (75.4 MHz) spectra of 1-(2,4,5-trimethoxy)phenyl-1-hydroxypropane in CDCl$_3$

PROCESS FOR THE PREPARATION OF PHARMACOLOGICALLY ACTIVE α-ASARONE FROM TOXIC β-ASARONE RICH *ACORUS CALAMUS* OIL

FIELD OF THE INVENTION

The present invention relates to "a process for the preparation of pharmacologically active α-asarone from toxic β-asarone rich *Acorus calamus* oil via intermediate 2,4,5-trimethoxyphenylpropane of the formula I (a dihydro product of toxic β-asarone) which is obtained via hydrogenation of commercially available *Acorus calamus* oil rich in β-asarone containing α and γ isomer), undergoes dehydrogenation and/or oxidation in a single step by just varying reaction time, temperature, solvent (anhydrous) and amount of dichlorodicyanobenzoquinone (DDQ) with or without a solid support such as silica gel, alumina and the like towards formation of α-asarone (trans-2,4,5-trimethoxyphenyl-1-propene), a well known pharmacolocally active phenylpropanoid, and trans-2,4,5-trimethoxycinnamaldehyde as a side product. However, above dehydrogenation process when conducted in aqueous solvent provides 1-(2,4,5-trimethoxy)phenyl-1-propanone which upon reduction with sodium borohydride into 1-(2,4,5-trimethoxy)phenyl-1-hydroxypropane followed by acidic dehydration affords α-asarone exclusively. Moreover, it is worthwhile to mention that 1-(2,4,5-trimethoxy)phenyl-1-propanone (isoacoramone) and 2,4,5-trimethoxycinnamaldehyde are found as phenylpropanoids present in traces in some of the aromatic and medicinal plants. Overall, the aim of this invention is to utilize internationally banned, but widely available toxic β-asarone as a simple and economical starting material for the preparation of a potential hypolipidemic and antiplatelet active α-asarone via combination of two simple industrially attractive processes i.e. hydrogenation and dehydrogenation/oxidation in which formation of the unexpected 2,4,5-trimethoxycinnamaldehyde is discovered as a side product during preparation of α-asarone. In the present invention, we have disclosed a simple and economical process that is capable of converting toxic β-asarone into pharmacological active α-asarone in high yield without contamination of its other isomers i.e. and/or γ-asarone.

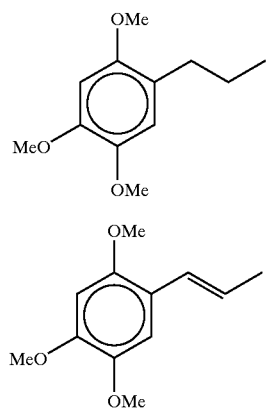

BACKGROUND OF THE INVENTION

Although the plant derived products have found widespread applications in the field of essential oils, colours and dyes, cosmetics, pharmaceuticals and in many others, not only because they are easily available and are cheaper but also an important reason has been the notion that they are safer than synthetic products, which may not always be true. There are several phytochemicals which beyond a certain limit, diminishes the market potential of products such as phenylpropanoids rich essential oils which get deteriorated specifically by few isomeric forms of phenylpropenes (Miller, E. C.; Swanson, A. B.; Phillips, D. H.; Fletcher, T. L.; Liem, A. and Miller, J. A., Cancer Research, 43 (3), 1124–1134 (1983); Kim; S. C.; Liem; A.; Stewart; B. C. and Miller, J. A. Carcinogensis, 20 (7), 1303–1307 (1999) and Lazutka, J. R.; Mierauskiene, S. and Dedonyte, V. Food & Chemical Technology, 39, 485–492 (2001)). In fact, phenylpropenes are naturally occurring phenolic compounds wherein an aromatic ring is attached to three-carbon side chain ($C_6$–$C_3$ unit), exist either as pair of cis/trans (i.e. α/β-isomer) propenyls or allyl propenes (i.e. γ-isomer). Generally, trans-isomers (e.g. α-asarone and isoeugenol etc) are found safer for human consumption while cis/allyl-isomers (e.g. β-asarone and saffrole) are found toxic and carcinogenic (Harborne, J. B. and Baxter, H., Phytochemical Dictionary: A Handbook of Bioactive Compounds from Plants, Taylor & Francis Ltd., Washington D.C., 474 (1993)). The concentration of phenylpropenes and their isomeric ratio in essential oils is greatly affected by growth stages and habitat of the plant, which in turn affect the demand and application of particular oil. Due to this, the most affected oil is calamus oil obtained by steam distillation of rhizomes of *Acorus calamus* (family: Araceae) which grows wildly and also cultivated in many countries due to its varied medicinal properties and great demand of its essential oil in flavour and perfumery industries (Treben, M., Health Through God's Pharmacy, Wilhelm Ennthaler, Steyer, Austria, 12–14 (1986); Akhtar, H.; Virmani, O. P.; Popli, S. P.; Misra, L. N.; Gupta, M. M.; Srivastava, G. N.; Abraham, Z. and Singh, A. K., Dictionary of Indian Medicinal Plants, CIMAP, RSM Nagar, Lucknow, 10–11 (1992); Motley, T. J., Economic Botany, 48, 397–412 (1994) and Lawrence, B. M. and Reynolds, R. J., Perfumer & Flavorist 22 (2), 59–67 (1997)). However, a lot of discrepancy and variability in quality of *calamus* oil has been observed in which tetraploid and hexaploid varieties (distributed extensively in Asian countries like India, Japan, Pakistan and China) contains a very high percentage of toxic β-asarone (varying from 70 to 90%) while diploid and triploid varieties contain limited amount of β-asarone (3 to 8%) which are allowed for use in flavor, perfumery and pharmaceutical industries (Stahl, E. and Keller, K., Planta Medica 43, 128–140 (1981); Waltraud, G. and Schimmer, O., Mutation Research 121, 191–194 (1983); Mazza, G., J. of Chromatography, 328, 179–206 (1985); Nigam, M. C.; Ateeque, A.; Misra, L. N. and Ahmad, A., Indian Perfumer, 34, 282–285 (1990) and Bonaccorsi, I.; Cortroneo, A.; Chowdhury, J. U. and Yusuf, M., Essenze Derv. Agrum., 67(4), 392–402 (1997)).

β-asarone is experimentally proved to be carcinogenic in animals and has also been found to induce tumors in the duodenal region after oral administration. In addition, β-asarone has also shown chromosome damaging effect on human lymphocytes in-vitro after metabolic activation (Taylor, J. M.; Jones, W. I.; Hogan, E. C.; Gross, M. A.; David, D. A. and Cook, E. L., Toxicol. Appl. Pharmacol., 10, 405 (1967); Keller, K.; Odenthal, K. P. and Leng, P. E., Planta Medica 1, 6–9 (1985); Abel, G., Planta Medica, 53(3), 251–253 (1987) and Riaz, M.; Shadab, Q.; Chaudhary, F. M., Hamdard Medicus, 38(2), 50–62 (1995)). As a result, the calamus oil of Asian origin is internationally banned for any kind of use in flavor, perfumery and pharmaceutical industries. To the best of our knowledge, there is no report in which toxic β-asarone of calamus oil is utilized for its value addition except very recently by our group (Sinha, A. K.; Dogra, R. and Joshi, B. P., Ind. J. Chem., 41B, (2002) (in press); Sinha, A. K.; Joshi, B. P. and Dogra, R., Nat. Prod. Lett., 15(6), 439–444 (2001); Sinha, A. K.; Acharya, R. and Joshi, B. P., J. Nat. Prod. (2002) (in press), Sinha, A. K.; Dogra, R. and Joshi, B. P., Sinha, A. K.; Joshi, B. P., and Dogra, R., JP Patent No. 2001.68716 filed on Mar. 12, 2001; Sinha, A. K.; Joshi, B. P., and Dogra, R., U.S. patent application Ser. No. 09/805,832 filed on Mar. 14, 2001; U.S. patent application Ser. No. 09/823,123 filed on Mar. 31, 2001 and Sinha, A. K.; Joshi, B. P., and Dogra, R., PCT/IN 01/00104 filed on May 21, 2001) wherein ammonium formate/palladium-on-charcoal or $H_2$/palladium-on-charcoal assisted reduction of crude *calamus* oil containing high percentage of toxic β-asarone provides 2,4,5-trimethoxyphenylpropane (dihydro asarone) in 97% purity with yield ranging from 81–87% based on asarones content in *calamus* oil (Example I). Thus, obtained 2,4,5-trimethoxyphenylpropane (also known as 1-propyl-2,4,5-trimethoxybenzene) is invented for the first time as five times less toxic than β-asarone and thus, this 2,4,5-trimethoxyphenylpropane enables its application in the products such as mouthwashes, tooth pastes, antiseptic soap products, chewing gum flavors and little in spicy products due to its sweet, ylang, slightly spicy and fruity aroma. In addition, 2,4,5-trimethoxyphenylpropane is also discovered as a simple and an economical starting material for synthesis of a salicylamide based antipsychotic drug (5,6-dimethoxy-N[(1-ethyl-2-pyrrolidinyl)methyl]-3-propylsalicylamide) (Thomas, H.; Stefan, B.; Tomas, D. P.; Lars, J.; Peter, S.; Hakan, H. and Orgen, S. O., J. Med. Chem., 33, 1155–1163 (1990) and Sinha, A. K., U.S. patent application Ser. No. 09/652,376 filed on Aug. 31, 2000). In the present invention, we have extended the scope of further exploitation of 2,4,5-trimethoxyphenylpropane of the formula I as simple and economical starting material towards the formation of pharmacological active α-asarone of the formula II.

α-asarone (trans-2,4,5-trimethoxyphenyl-1-propene) is well known for its several pharmacological activities including hypolipideamic and antiplatelet activity but is generally present in traces with β and γ-asarone in various plant species including *A. calamus* (Patra, A. and Mitra, A. K., J. Nat. Prod., 44, 668–669 (1981); Dung, N. X.; Moi, L. D.; Nam, V. V.; Cu, L. D. and Leclercq, P. A., J. of Ess. Oil Res., 7 (1), 111–112 (1995) and Parmar, V. S.; Jain, S. C.; Bisht, K. S.; Jain, R.; Taneja, P.; Jha, A.; Tyagi, O. D.; Prasad, A. K.; Wengel, J.; Olsen, C. E.; Boll, P. M., Phytochemistry, 46 (4), 597–673 (1997)). Separation of less abundant α-asarone is particularly difficult via column chromatography of asarones rich essential oil. Although, few methods are found in literature for the synthesis of α-asarone including alkaline isomerisation of γ-asarone (2,4,5-trimethoxyallylbenzene), however, a little amount of toxic β-asarone is always present with α-asarone during alkaline isomerization (Devgan, O. N. and Bokadia, M. M., Aust. J. Chem., 21, 3001–3003 (1968)). Thus, the reported synthetic methods are not free from drawbacks such as multisteps approach, expensive reagents and overall poor yield with contamination of its isomers. In view of these problems two factors are pivotal for the synthesis of α-asarone, first to achieve highest selectivity for the formation of α-isomer without any presence of other isomers and secondly, search for simple, economical and efficient methods to obtain α-asarone which can be easily achieved by dehydrogenation of 2,4,5-trimethoxyphenylpropane with the help of dehydrogenating reagents such as 2,3-dichloro-5,6-dicyano-1,4-benzoquinone (DDQ). Among dehydrogenating agents namely, manganese dioxide, p-chloranil, selenium dioxide, Pd/C, selenium and sulphur, DDQ is invented as a single reagent of choice towards formation of α-asarone in a single step by just varying reaction time, temperature, solvent and amount of reagent (DDQ) with or without a solid support such as silica gel, alumina and the like in a mono or biphasic system. In anhydrous solvents namely, alcohol such as methanol, ethanol and the like; aliphatic and aromatic hydrocarbons such as hexane, benzene, toluene and the like; ether such as tetrahydrofuran, dioxane and the like, the reaction between 2,4,5-trimethoxyphenylpropane and varying amount of DDQ, preferably ranging from 1.0 to 1.1 moles, furnishes the corresponding dehydrogenated product i.e. trans-asarone (α-asarone) in 41–44% yield and unreacted starting material (i.e. 2,4,5-trimethoxyphenylpropane) along with yellow coloured compound as a side product (4–6%) while 2,4,5-trimethoxyphenylpropane and varying amount of DDQ, preferably ranging from 1.1 to 1.3 moles, furnishes α-asarone (48–51%) as well as above yellow coloured compound (9–11%) but without any starting material (Example II). It is interesting to note that the addition of a catalytic amount of solid support such celite, silica gel, alumina, resin and the like to the above mixtures of 2,4,5-trimethoxyphenylpropane and DDQ (1.1 to 1.3 moles) dramatically accelerates the rate of dehydrogenation as well as increases the yield of α-asarone (67–72%) (Example III). On the basis of IR, NMR, Mass spectral data, yellow solid is found to be trans-2,4,5-trimethoxycinnamaldehyde which was further confirmed by comparing the mixed m.p. (139–140° C.) of standard trans-2,4,5-trimethoxycinnamaldehyde prepared by reaction of α-asarone (trans-asarone, procured from Sigma Chemical Ltd.) with DDQ in dioxane. Further, trans-2,4,5-trimethoxycinnamaldehyde has appeared as a rare phenylpropanoid present in *Caesulia axillaries* and *Alpinia flabella* (0.000015%) in traces (Kulkarni, M. M.; Sohoni, J.; Rojatkar, S. R. and Nagasampagi, B. A., Ind. J. Chem. Sec. B 25B, 981–982 (1986) and Kikuzaki, H.; Tesaki, S.; Yonemori, S. and Nakatani, N. Phytochemistry, 56(1), 109–114 (2001), thus, preparation of trans-2,4,5-trimethoxycinnamaldehyde in sufficient quantity opens new vistas for the evaluation of its various applications known for structurally similar cinnamaldehyde derivatives (Tomoshi, K. and Makoto, F., JP Pat. No. 58055414A2; Saotome, K., JP Pat. No. 58201703A2; Watanabe, T., Komeno, T. and Hatanaka, M., JP Pat. No. 6312916A2 and Castelijns, A. M. C. F., Hogeweg, J. M. and vanNispen, S. P. J. M., U.S. Pat. No. 5,811,588)). After having confirmed the structure of α-asarone and trans-2,4,5-trimethoxycinnamaldehyde, our attention was focused towards exclusive formation of α-asarone in high yield without any starting material and yellow side product (i.e. 2,4,5-trimethoxycinnamaldehyde).

An alternate route for the synthesis of α-asarone is appeared via 1-(2,4,5-trimethoxy)phenyl-1-propanone which can be easily prepared by treating 2,4,5-trimethoxyphenylpropane with varying amount of DDQ (1.0 to 3 moles), preferably ranging from 1.6 to 2.1 moles, in an aqueous organic solvent selected from methanol, ethanol, tetrahydrofuran, dioxane and the like. Later on, 2,4,5-trimethoxypropiophenone (isoacoramone) is realized as an interesting rare phenylpropanoid occurring in well known medicinal plant *Acorus calamus, Piper marginatum* as well as in *Acorus tararinowii* but only in traces (Mazza, G., J. of Chromatography, 328,179–206 (1985); Santos, B. V. de O. and Chaves, M. C. de O., Biochem. Systematics Ecology, 25, 539–541 (1999) and Jinfeng, Hu and Xiaozhang, Feng, Planta Medica, 66, 662–664 (2000). Thus, formation of 2,4,5-trimethoxypropiophenone (isoacoramone) not only appeared as a synthon for the preparation of α-asarone but also facilitate its more rigorous biological evaluation known for structurally similar propiophenone derivatives (Stauffer, S. R.; Coletta, C. J.; Tedesco, R.; Nishiguchi, G.; Carlson, K.; Sun, J.; Katzenellenbogen, B. S. and Katzenellenbogen, J. A., J. Med. Chem., 43, 4934–4947 (2000) and Jaimol, T.; Moreau, P.; Finiels, A.; Ramaswamy, A. V. and Singh, A. P., Applied Catalysis A: General, 214, 1–10 (2001)). To obtain a α-asarone, 1-(2,4,5-trimethoxy)phenyl-1-propanone is reduced with sodium borohydride into (1-(2,4,5-trimethoxy) phenyl-1-hydroxypropane) followed by acidic dehydration using either p-toluenesulphonic acid or thionyl chloride/ pyridine and the like (Example IV–VI).

In conclusion, our invention discloses a simple and economical process for the preparation of pharmacologically active α-asarone along with two important naturally occurring phenylpropanoids namely 2,4,5-trimethoxypropiophenone (isoacaromone) and 2,4,5-trimethoxycinnamaldehyde, starting from relatively cheaper and economical material 2,4,5-trimethoxyphenylpropane obtained via hydrogenation of β-asarone rich *Acorus calamus* oil as outlined in Scheme-I. Other objectives and advantages of the present invention will be made apparent as the description progresses.

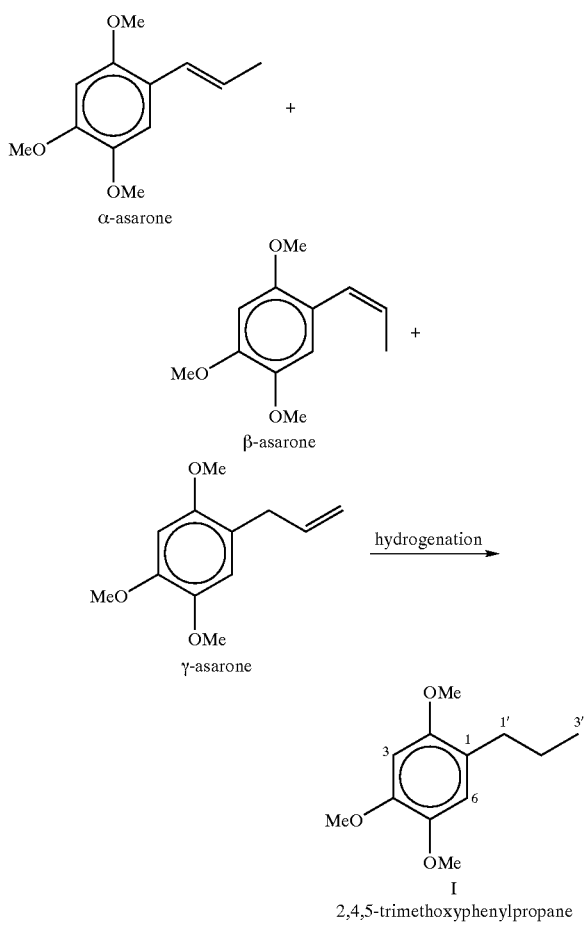

Scheme-I

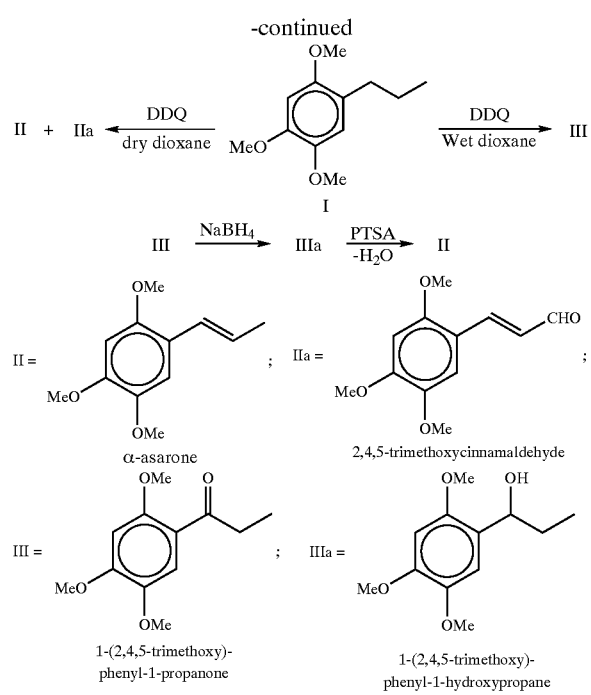

OBJECTIVES OF THE INVENTION

The main object of the present invention is to prepare pharmacologically active α-asarone from 2,4,5-trimethoxyphenylpropane which is, in fact, is a hydrogenated product of toxic β-asarone isolated from commercially available *Acorus calamus* oil.

Another object of the present invention is to explore the possibilities of utilizing toxic *calamus* oil of tetraploid or hexaploid varieties (distributed extensively in Asian countries), thereby, enhancing the profitable use thereof.

Still another object of the invention is to develop a simple process for the preparation of α-asarone exclusively without any contamination of other isomeric forms of asarone (i.e. β and/or γ-isomer).

Yet another object of the invention is to develop a process for the preparation of a non-toxic compound i.e. α-asarone from toxic compound i.e. β-asarone.

Yet another object of the invention is to study the interaction of 2,4,5-trimethoxyphenylpropane by varying time, temperature, solvents and amount of dehydrogenating reagent DDQ.

Yet another object of the invention is to use DDQ as a dehydrogenating reagent for the first time for the preparation of α-asarone exclusively from 2,4,5-trimethoxyphenylpropane.

Yet another object of the invention is to develop easy purification process to obtain α-asarone in high purity as well as in good yield.

Yet another object of the invention is to characterize the unexpected formation of polar yellow solid, which, in fact, formed as a side product along with α-asarone.

Yet another object of the invention is to establish the structure of yellow solid which finally appeared to be a naturally occurring rare trans-2,4,5-trimethoxycinnamaldehyde.

Yet another object of the invention is to develop another route for the preparation of α-asarone starting from 1-(2,4, 5-trimethoxy)phenyl-1-propanone.

Yet another object of the invention is to prepare 1-(2,4,5-trimethoxy)phenyl-1-propanone (isoacoramone) by treating 2,4,5-trimethoxyphenylpropane with DDQ in aqueous organic solvent.

Yet another object of the invention is to prepare α-asarone exclusively via reduction of 1-(2,4,5-trimethoxy)phenyl-1-propanone into corresponding 1-(2,4,5-trimethoxy)phenyl-1-propanol followed by the acidic dehydration.

SUMMARY OF THE INVENTION

The present invention provides a process for the preparation of pharmacologically active natural occurring α-asarone utilizing combination of 2,3-dichloro-5,6-dicyano-1,4-benzoquinone (DDQ) as mild and efficient dehydrogenating agent and 2,4,5-trimethoxyphenylpropane which is, in fact, the hydrogenated product of toxic β-asarone isolated from commercially available *calamus* oil. It is worthwhile to mention that the above DDQ assisted dehydrogenation process not only led to α-asarone but also provided two more products which later on were characterized as naturally occurring rarer phenylpropanoids namely 2,4,5-trimethocyphenylpropanone (isoacoramone) and 2,4,5-trimethoxycinnamaldehyde. Therefore, formation of α-asarone, isoacoramone and 2,4,5-trimethoxycinnamaldehyde in one step process via DDQ assisted dehydrogenation/oxidation of 2,4,5-trimethoxyphenylpropane, is a cheaper and economical method than so far reported methods, as well as, our invention is capable of forming a series of biologically active phenylpropanoids derivatives.

BRIEF DESCRIPTION OF THE ACCOMPANYING DRAWINGS

Figure 1:
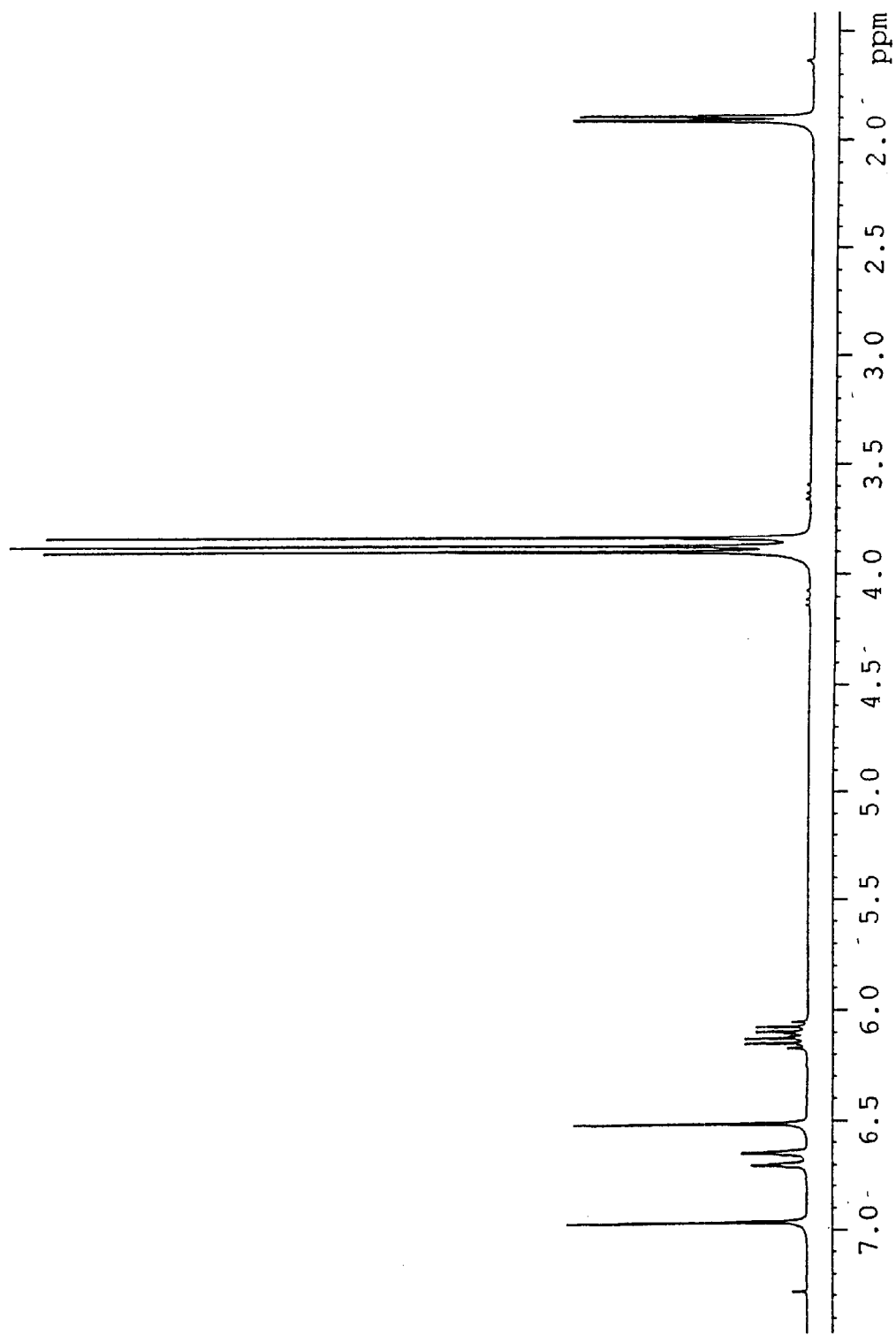
FIG. 1 is $^1$H NMR (300 MHz) spectra of α-asarone (in $CDCl_3$) of the reaction product of Example II.
Figure 2:
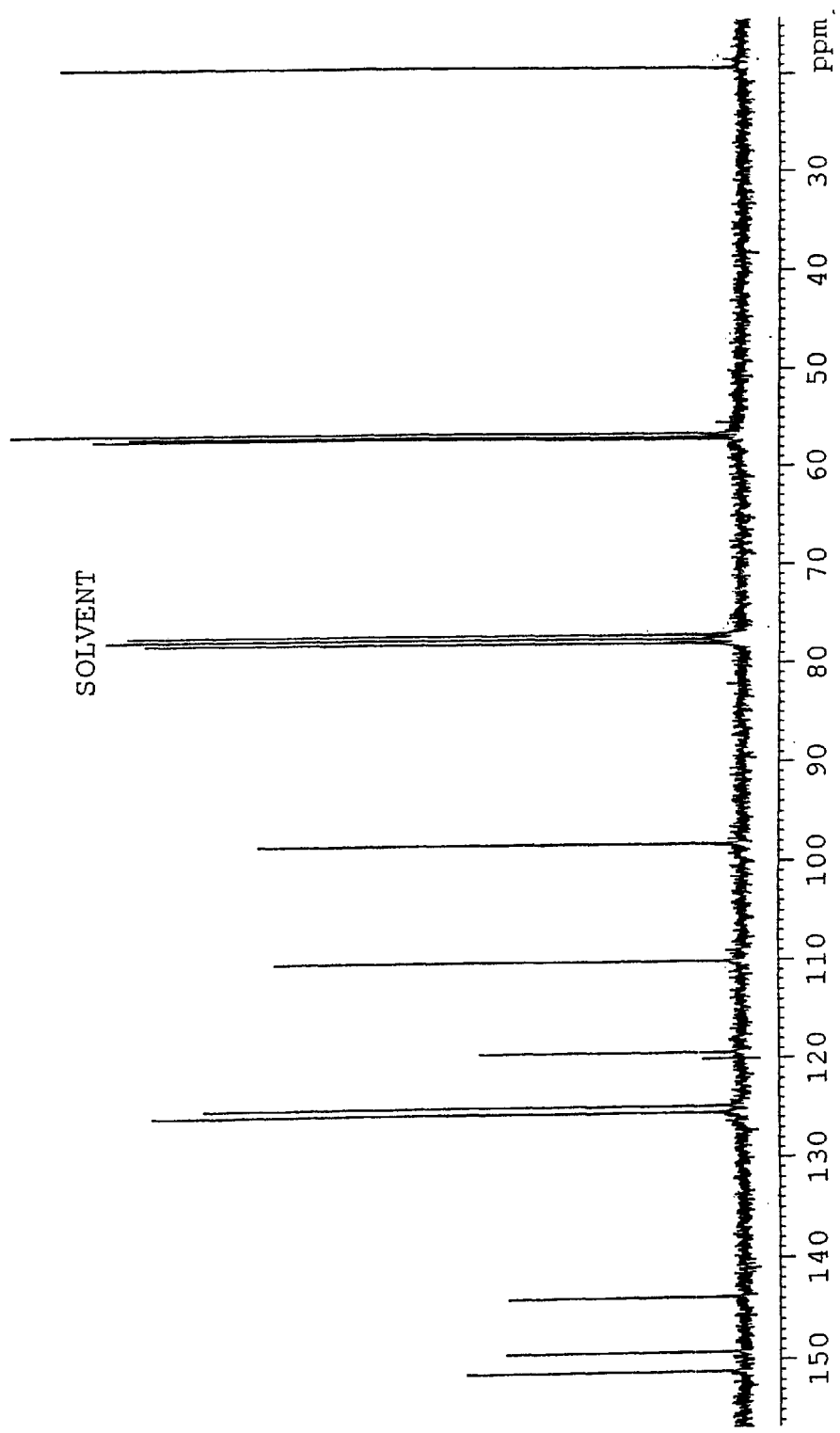
FIG. 2 is $^{13}$C NMR (75.4 MHz) spectra of α-asarone (in $CDCl_3$) of the reaction product of Example II.
Figure 3:
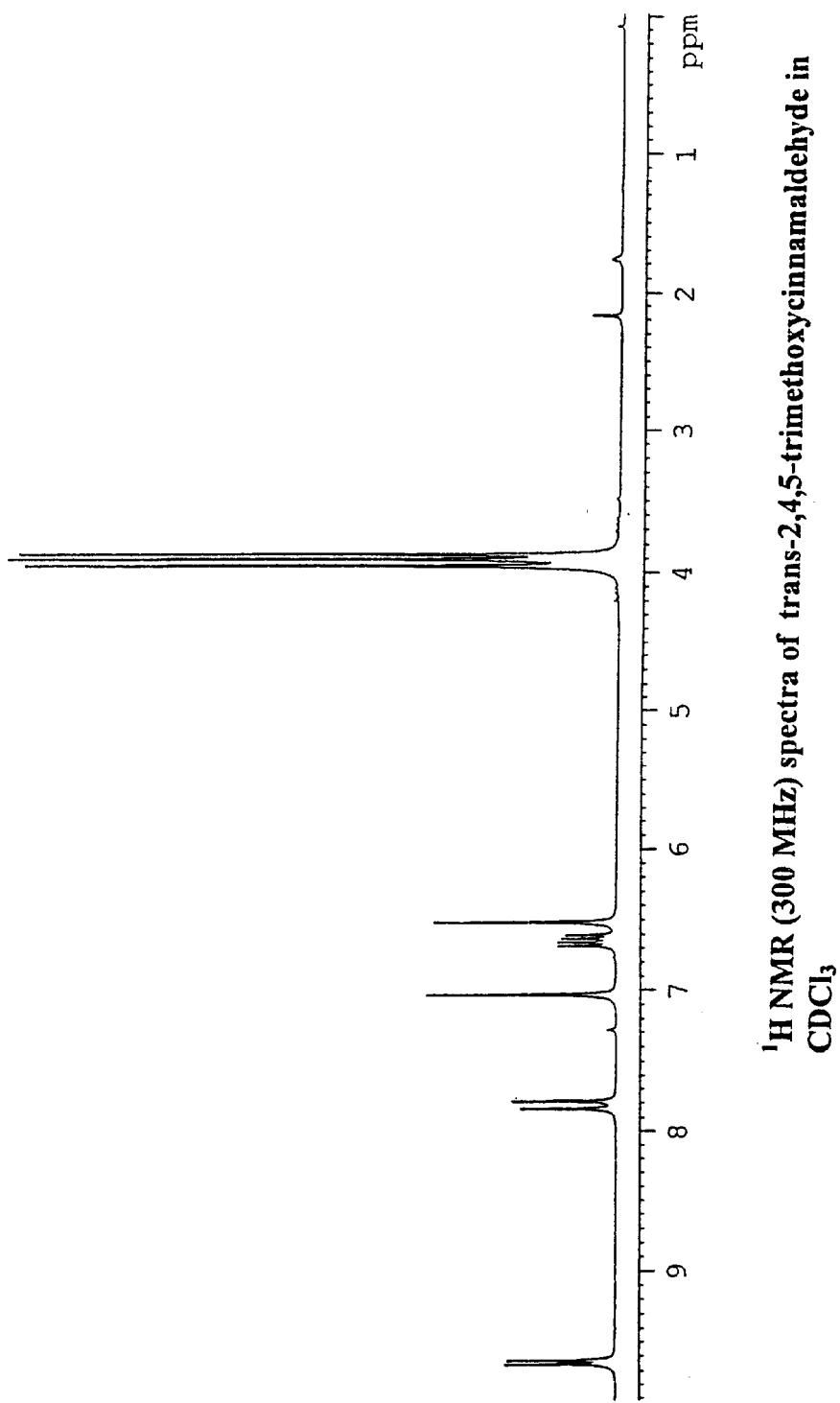
FIG. 3 is $^1$H NMR (300 MHz) spectra of 2,4,5-trimethoxycinnamaldehyde (in $CDCl_3$) of the reaction product of Example III.
Figure 4:
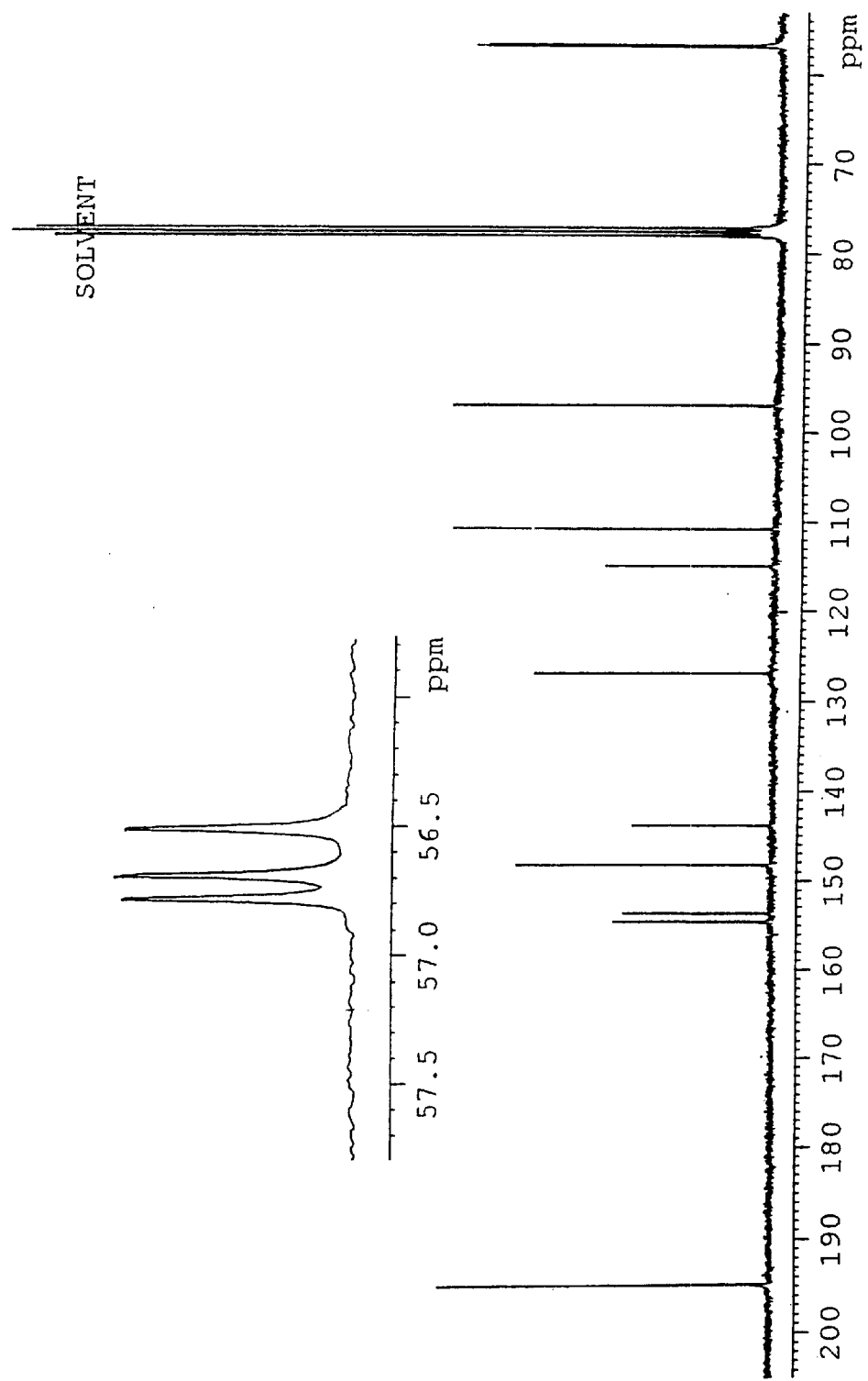
FIG. 4 is $^{13}$C NMR (75.4 MHz) spectra of 2,4,5-trimethoxycinnamaldehyde (in $CDCl_3$) of the reaction product of Example III.
Figure 5:
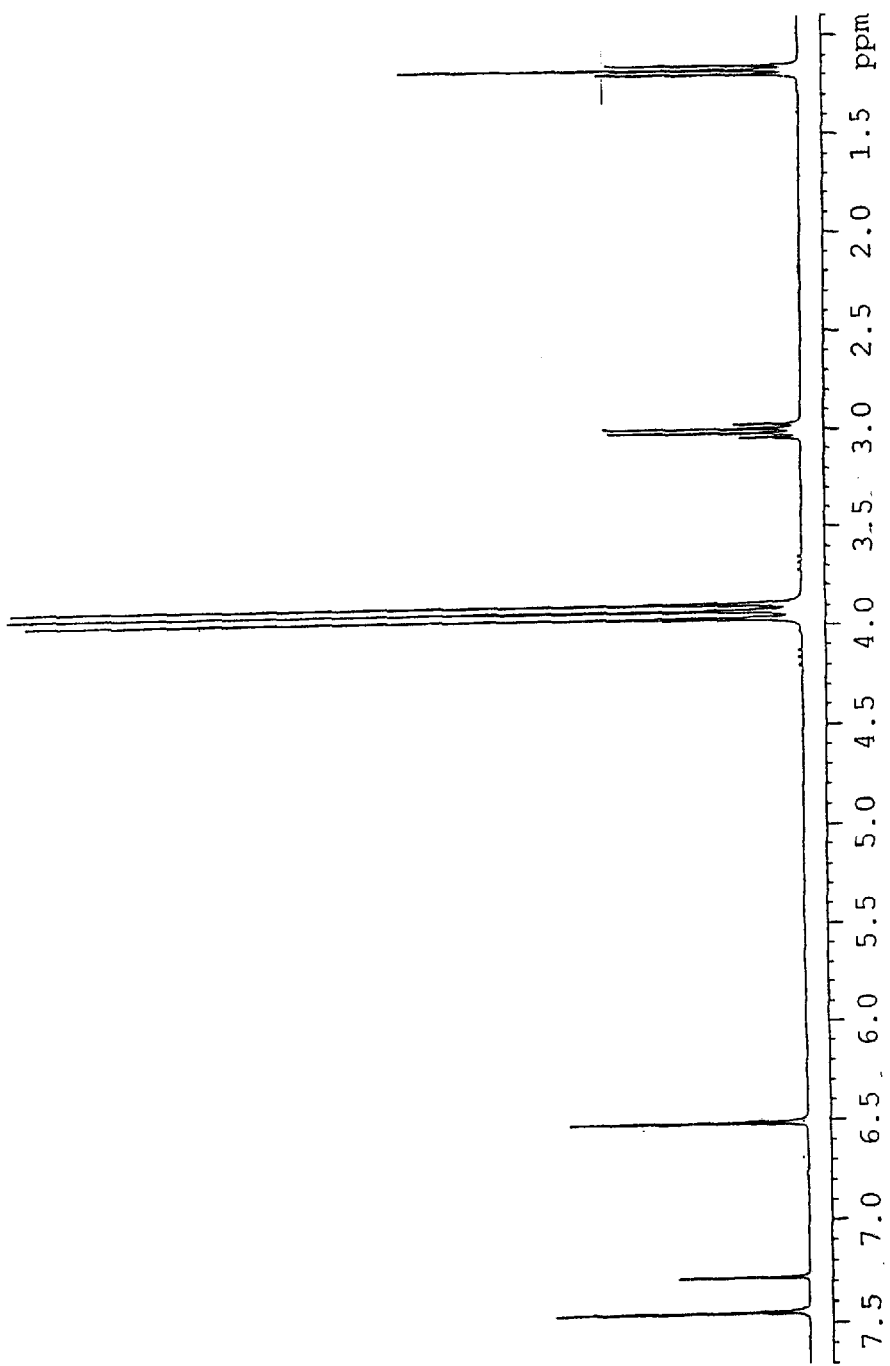
Figure 6:
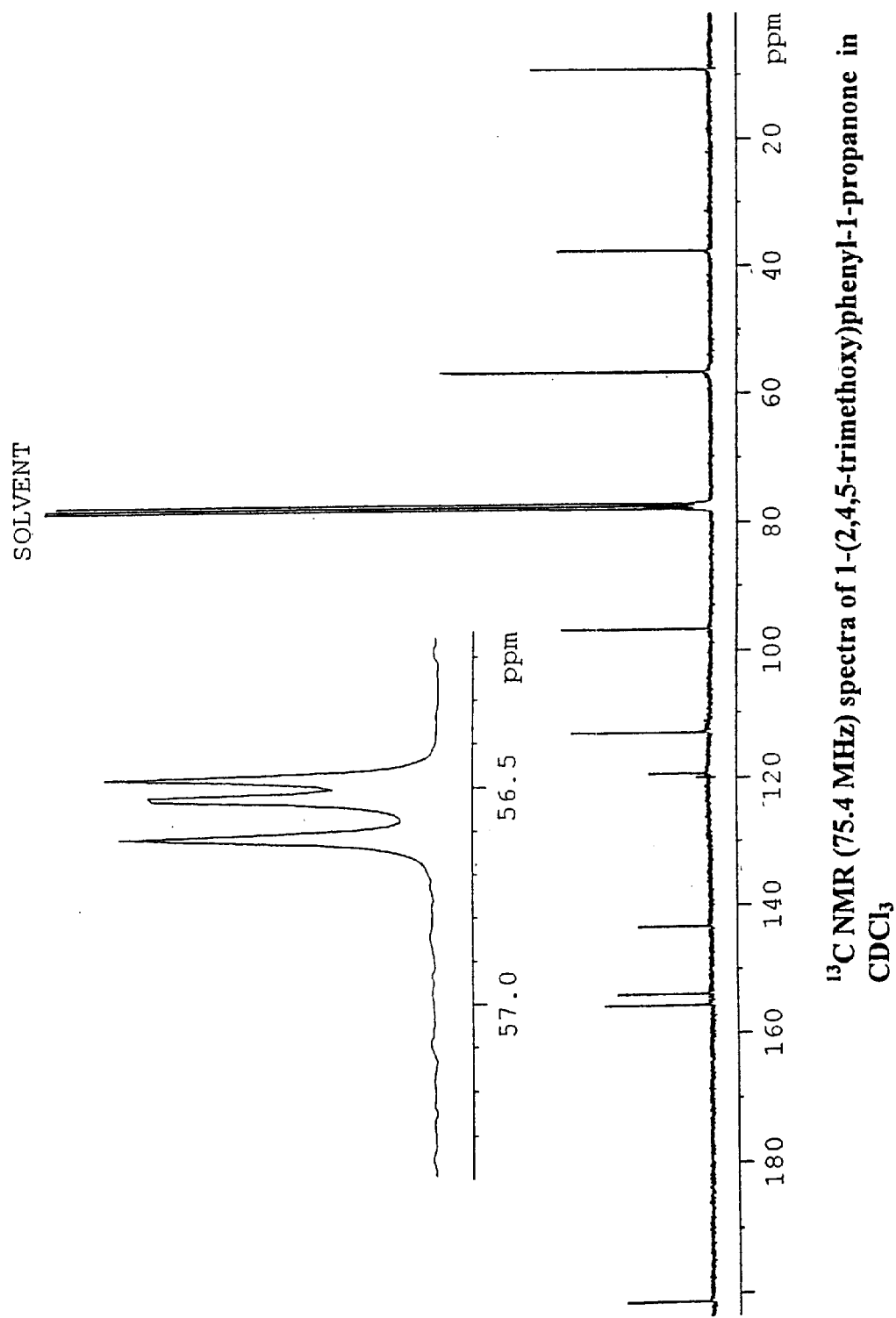
Figure 7:
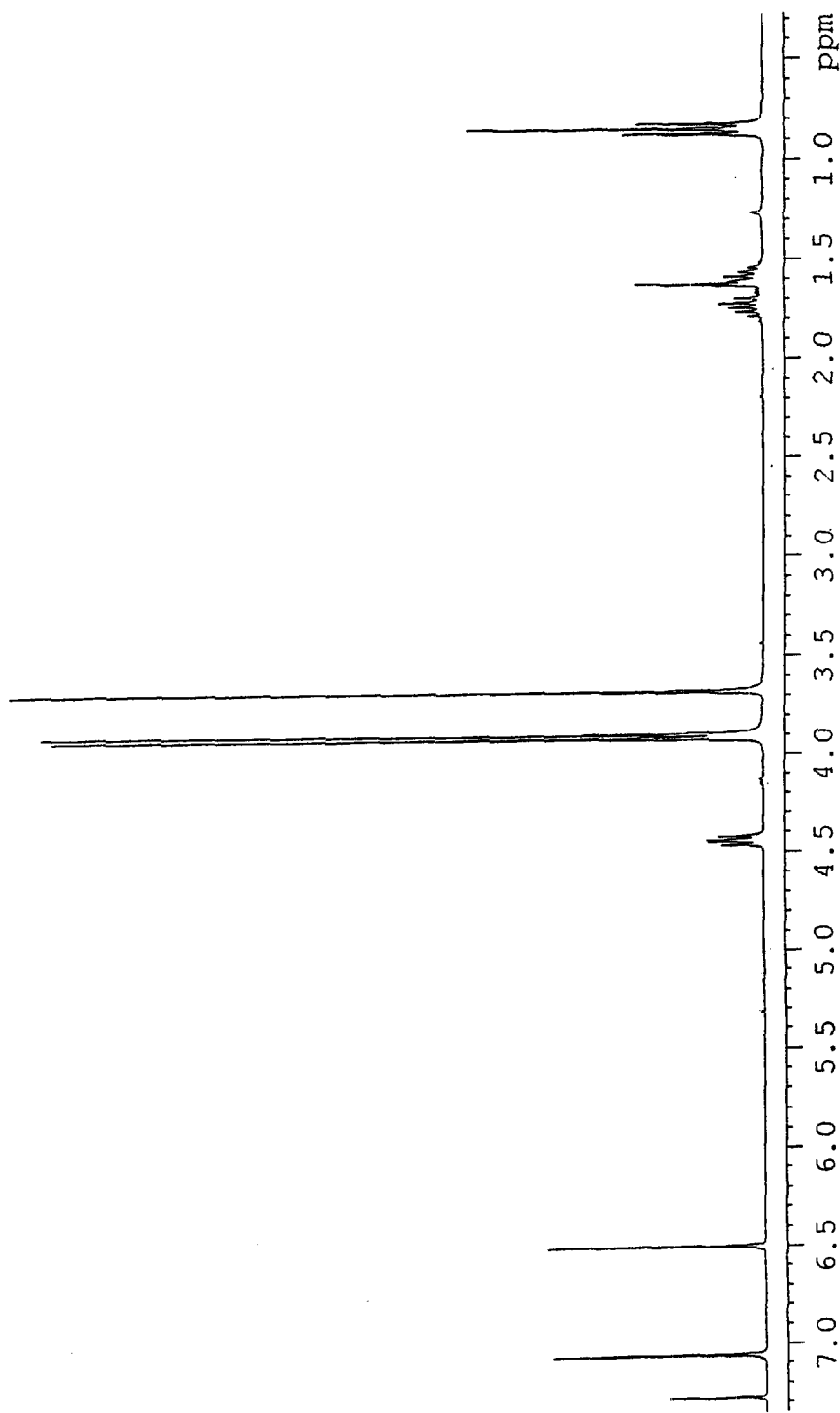
Figure 8:
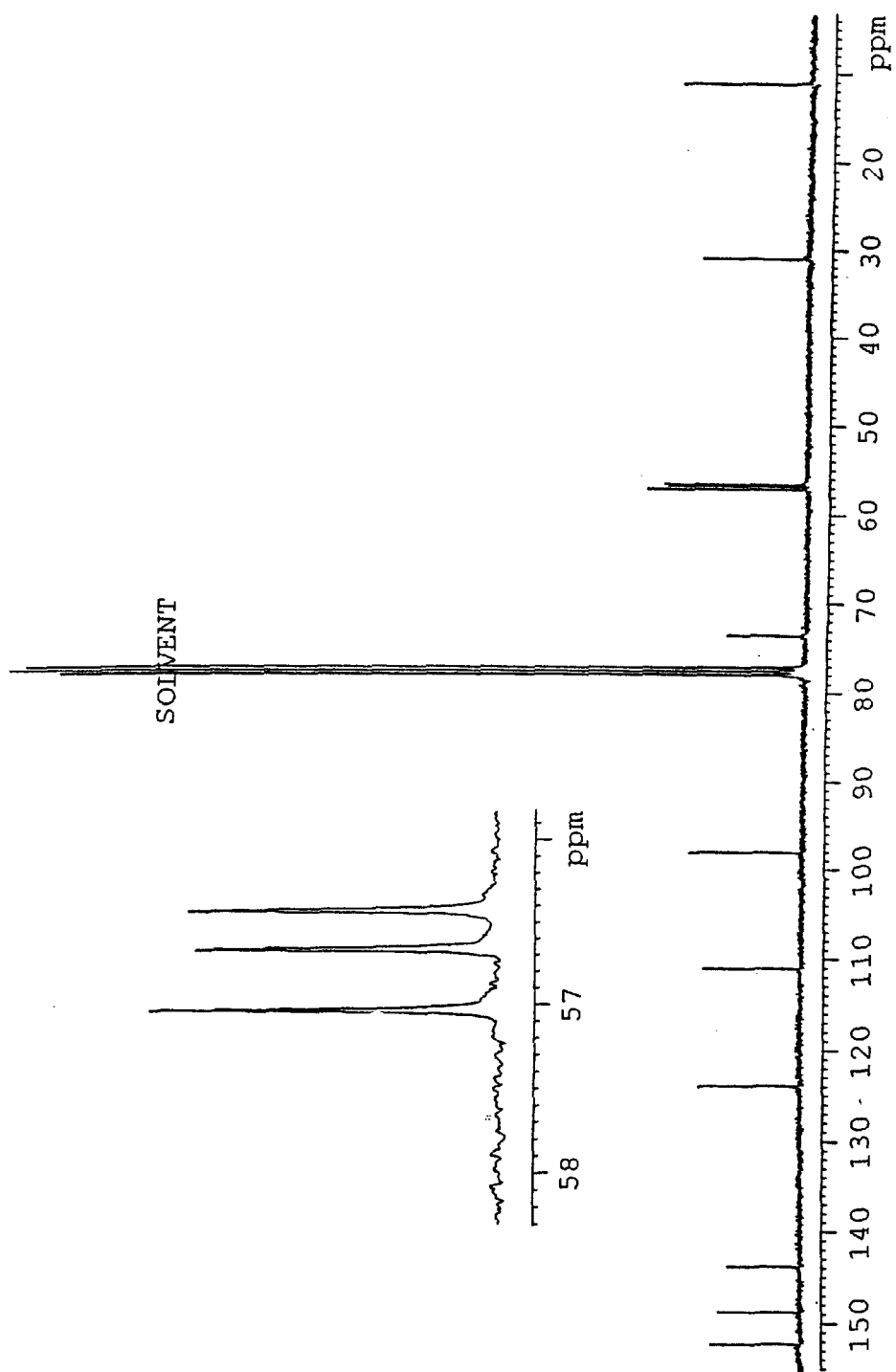

FIG. 5 is $^1$H NMR (300 MHz) spectra of 1-(2,4,5-trimethxy)phenyl-1-propanone (in $CDCl_3$) of the reaction product of Example IV FIG. 6 is $^{13}$C 300 MHz) spectra of 1-(2,4,5-trimethxy)phenyl-1-propanone (in $CDCl_3$) of the reaction product of Example IV FIG. 7 is $^1$H NMR (300 MHz) spectra of 1-(2,4,5-trimethxy)phenyl-1-hydroxypropane (in $CDCl_3$) of the reaction product of Example V FIG. 8 is $^{13}$C 300 MHz) spectra of 1-(2,4,5-trimethxy)phenyl-1-hydroxypropane (in $CDCl_3$) of the reaction product of Example V

DETAILED DESCRIPTION OF THE INVENTION

Accordingly, the present invention provides "a process for the preparation of pharmacologically active α-asarone from toxic β-asarone rich *Acorus calamus* oil via intermediate 2,4,5-trimethoxyphenylpropane" wherein the said process comprises hydrogenation of toxic β-asarone or calamus oil containing a mixture of α, β and γ-asarone to obtain 2,4,5-trimethoxyphenylpropane of the formula I followed by the dehydrogenation of the above said compound at a temperature in the range of 5–120° C. for a period ranging from 30 minutes to 72 hours using solvent.

In an embodiment of the present invention, a simple process is available to prepare pharmacologically active α-asarone from 2,4,5-trimethoxyphenylpropane, which is, in fact, the hydrogenated product of toxic β-asarone isolated from commercially available *calamus* oil.

In another embodiment of the present invention, a simple process is available for the commercial utilization of internationally banned but widely available toxic β-asarone from *Acorus calamus* oil of tetraploid or hexaploid varieties (distributed extensively in Asian countries), thereby, enhancing the profitable use thereof.

In still another embodiment of the present invention, a simple process involves the conversion of mixture of all the three isomeric forms of phenylpropene i.e. α,β and γ-asarone firstly into 2,4,5-trimethoxyphenylpropane and then regenerating 1-(2,4,5-trimethoxy)phenyl-1-propene derivative exclusively in trans form (α-asarone).

In another embodiment of the present invention, a simple process is available for the preparation of α-asarone exclusively without any contamination of other isomeric forms of asarone (i.e. β and/or γ-isomer).

In yet another embodiment of the present invention, a simple process is available for the preparation of less toxic compound (i.e. α-asarone) from a known toxic compound (β-asarone).

In yet another embodiment of the present invention, a simple process which discloses the interaction of 2,4,5-trimethoxyphenylpropane with varying amount of dehydrogenating reagent such as DDQ and also varying time, temperature and solvents.

In yet another embodiment of the present invention, provides α-asarone from 2,4,5-trimethoxyphenylpropane for the first time using mild dehydrogenating reagent DDQ.

In yet another embodiment of the present invention, the molar ratio of dehydrogenating agent (DDQ) to 2,4,5-trimethoxyphenylpropane is used in the ratio of 1.0:1.0 to 1.3:1.0 preferably 1.0 to 1.2:1.0.

In yet another embodiment of the present invention, provides an easy purification process to obtain α-asarone in good yield.

In yet another embodiment of the present invention, to characterize the unexpected formation of polar yellow solid which finally appeared to be naturally occurring rare trans-2,4,5-trimethoxycinnamaldehyde.

In yet another embodiment of the present invention, provides semi-synthetic route for α-asarone with high yield which is capable of manufacturing on industrial scale.

In yet another embodiment of the present invention, provides 2,4,5-trimethoxyphenylpropanone exclusively by treating 2,4,5-trimethoxyphenylpropane with DDQ in organic solvent selected from methanol, dioxane, THF and water in the ratio ranging from 9.9:0.1 to 9:1 and at a temperature in the range of 5–110° C. preferably 8–60° C.; reaction period of time is 1 hour to 54 hours, preferably 6–18 hours.

In yet another embodiment of the present invention provides 2,4,5-trimethoxypropiophenone as a solid compound whereas, natural 2,4,5-trimethoxypropiophenone (isolated from *Acorus tatarinowii* and *Piper marginatum*) is reported as viscous gum.

In yet another embodiment of the present invention, provides natural 2,4,5-trimethoxypropiophenone in sufficient quantity, which further provides the opportunity for its wide range of biological evaluation.

In yet another embodiment of the present invention, provides a process for the preparation of α-asarone from 2,4,5-trimethoxypropiophenone via its reduction into 1-(2,4,5-trimethoxy)phenyl-1-hydroxypropane followed by dehydration under acidic condition.

In yet another embodiment of the present invention, dehydration of 2,4,5-trimethoxyphenyl-1-hydroxypropane is carried out with p-toulene sulphonic acid and thionyl chloride/pyridine and the like provides α-asarone.

Phenylpropanoids ($C_6$–$C_3$) are mainly produced in plants in response to pathogen attack. This group of secondary metabolites comprises many biologically active compounds like phenylpropanones, cinnamaldehydes, cinnamal alcohols, cinnamic acids and phenylpropenes. Among three isomeric forms of phenylpropene, cis and γ-isomeric forms have proved to be toxic and carcinogenic while trans-isomeric form is reported for its use in flavour, perfumery and pharmaceutical industries but generally trans-isomer is often present in little percentage in plant kingdom (Miller, E. C.; Swanson, A. B.; Phillips, D. H.; Fletcher, T. L.; Liem, A. and Miller, J. A., Cancer Research, 43 (3), 1124–1134 (1983); Kim; S. C.; Liem; A.; Stewart; B. C. and Miller, J. A. Carcinogensis, 20 (7), 1303–1307 (1999) and Lazutka, J. R.; Mierauskiene, S. and Dedonyte, V. Food & Chemical Technology, 39, 485–492 (2001)). In spite of several synthetic methods, the alkaline isomerisation of γ-isomer leads to useful trans-isomer but always with a little percentage of toxic cis-isomer. So, it appeared quite interesting and challenging to develop a simple method for the preparation of trans-isomer exclusively using cis-isomer i.e. conversion of widely and commercially available toxic β-asarone (cis-isomer) towards synthesis of α-asarone (trans-isomer) since rarer α-asarone has a great potential and scope in the area of pharmaceutical industries as discussed in details below:

α-asarone (trans-2,4,5-trimethoxy-1-propenylbenzene), a constituent of *A. calamus* and several other plants (Enqiquez, R. G.; Chavez, M. A. ande Jauregui, F., Phytochemistry, 19 (9), 2024–2025 (1980) and Dung, N. X.; Moi, L. D.; Nam, V. V.; Cu, L. D. and Leclercq, P. A., J. of Ess. Oil Res., 7 (1), 111–112 (1995)), is well known for its pharmacological effects such as sedating, neuroleptic, spasmolytic, antiulcerogenic, antiatherogenic (Menon, M. K.; and Dandiya, P. C., J. Pharm. Pharmacol., 9 (3), 170–175 (1967) and Belova, L. F.; Alibekov, S. D.; Baginskaya, A. I.; Sokolov, S. Y. and Pokrovskava, G. V., Farmakol. Toksikol., 48, 17–20 (1985)) including hypolipidemic and antiplatelet activities (Janusz, P.; Bozena, L.; Alina, T. D.; Barbara, L.; Stanislaw, W.; Danuta, S.; Jacek, P.; Roman, K.; Jacek, C.; Malgorzata, S. and Zdzislaw, C., J. Med. Chem., 43, 3671–3676 (2000)). As per hypolipideamic activity is concerned, the available synthetic drugs used for decreasing the levels of cholesterol and triglyceride are Colestipol, Questran, Clofibrate and Neomycin etc which have a certain degree of side effects such as nausea, abdominal and gastrointestinal discomfort, constipation, brittle hair, diarrhea and heartburn. In particular, neomycin has found to have high toxicity. Thus, so far there is no effective and safe drugs which can decrease high cholesterol and triglyceride levels in the patients without side effects. On the other hand, the traditional natural herbs such as *Angelica sinesis, Artemisia capillaries, Curcuma longa* (Soudamini, K. K.; Unnikrishnan, M. C.; Soni, K. B. and Kuttan, R., Ind. J. Physiol. Pharmacol., 36, 239–243 (1992) and Deters, M.; Siegers, C.; Hansel, W.; Schneider, K. P. and Hennighausen, G., Planta Medica, 66, 429–434 (2000)) have been used in clinics for decreasing levels of hyperlipidemia. Similarly, the bark of *Guatteria gaumeri,* a traditional Maxican medicine, is also used to treat hypercholesterolaemia and cholelithiasis, and its active constituent is reported to be α-asarone (Gomez, C.; Chamorro, G.; Chav'ez, M. A.; Martinez, G.; Salazar, M.; Pages, N., Plant. Med. Phytother., 21, 279–284 (1987)). Cholesterol and triglycerides lowering activity was observed for α-asarone at an oral dose of 80 mg/kg in mice fed with a high cholesterol diet, showing a decrease of 49.6% and 83.7%, respectively. However, the high density lipoprotein (HDL)-cholesterol was found to be increased. (Hernandez, A.; Lopez, M. L.; Chamorro, G. and Mendoza, F. T., Planta Medica, 59 (2), 121–124 (1993); Chamorro, G.; Salazar, M.; Salazar, S. and Mendoza, F. T., Revista-de-Investigacion Clinica, 45 (6), 597–604 (1993) and Garduno, L.; Salazar, M.; Salazar, S.; Morelos, M. E.; Labarrios, F.; Tamariz, J. and Chamorro, G. A., J. of Ethnopharmacology, 55 (2), 161–163, (1997). Toxicity of α-asarone is also investigated in rats and mice and no toxic effect is observed (Salazar, M.; Salaz, S.; Ulloa, V.; Mendoza, T.; Pages, N. and Chamorro, G., J. Toxicol. Clin. Exp., 12, 149–154 (1992); Chamorro, G., Salazar, M.; Salazar, S. and Mendoza, T., Rev. Invest. Clin., 45, 592–604 (1993); Sagimoto, N.; Goto, Y.; Akao, N.; Kiucki, F. and Kondo, K., Biol. Pharm. Bull., 18, 605–609 (1995); Lopez, M. L.; Hernandez, A.; Chamorro, G. and Mendoza, F. T., Planta Medica, 59 (2), 115–120 (1993) and Chamorro, G. A.; Salazar, M.; Tamariz, J; Diaz, F. and Labarrios. F., Phytotheraphy Research, 13(4), 308–311 (1999)). In addition, α-asarone is also used as a starting material for the synthesis of various biologically active compounds (Mori-K; Komatsu, M; Kido, M and Nakagawa, K, Tetrahedron Letter, 42 (2), 523–528 (1986)) as well as in the formulation of drugs (Harborne, J. B. and Baxter, H. In: Phytochemical Dictionary: A Handbook of Bioactive Compounds from Plants, Taylor & Francis Ltd., Washington D.C., 474 (1993)). Conventionally, some synthetic routes have been developed to prepare α-asarone such as:

(a) a method utilizing trimethoxybenzene as the starting material (Francisco, D.; Leticia, C.; Rosa, F.; Joaquin, T.; Fernando, L.; German, C.; Heber, M. Org. Prep. Proced. Int. 23 (2), 133–138 (1991)).

(b) a method in which 2,4,5-trimethoxybenzaldehyde was treated with ethyl magnesium bromide (Grignard reagent) to afford corresponding alcohol and then dehydration of alcohol to α-asarone (Wang, Z.; Jiang, L. and Xingxiang, X., Youji Huaxue, 10 (4), 350–352 (1990); Shirokova, E. A.; Segal, G. M. and Torgov, I. V., Bioorg. Khim., 11 (2), 270–275 (1985) and Janusz, P.; Bozena, L.; Alina, T. D.; Barbara, L.; Stanislaw, W.; Danuta, S.; Jacek, P.; Roman, K.; Jacek, C.; Malgorzata, S. and Zdzislaw, C., J. Med. Chem., 43, 3671–3676 (2000)).

(c) A method utilizing vanillin as the starting material (Nenokichi, H. and Shibamoto, N., Kinki Daigaku Rikogakubu Kenkyu Hokoku, 12, 63–66 (1977)).

(d) a method comprising photochemical isomerisation of beta-asarone (Saxena, D. B. and Mukeijee, S. K., Indian J. of Chem., 24B, 683–684 (1985)).

However, all the above reported methods are not practical, because they require several steps, expensive reagents and starting materials with overall poor yield. In the continuing efforts towards synthesis of α-asarone with highest selectivity, two step process which involves hydrogenation of the widely and commercially avalaible β-asarone (as discussed above) into 2,4,5-trimethoxyphenylpropane (dihydro asarone) followed by dehydrogenation, appears to be free from the above mentioned drawbacks.

2,4,5-trimethoxyphenylpropane can be obtained by catalytic reduction of β-asarone or the like by hydrogenation process in paar reactor. However, hydrogenation in paar reactor requires explosive hydrogen gas cylinder and also, monitoring of the progress of reaction by TLC is not possible during the hydrogenation. Thus, we have recently reviewed the effectiveness of ammonium formate or formic acid/triethylamine as a catalytic hydrogen transfer agent for the first time for the reduction of plant derived β-asarone or β-asarone rich calamus oil towards formation of 2,4,5-trimethoxtphenylpropane (Sinha, A. K., U.S. patent application Ser. No. 09/652,376 filed on Aug. 31, 2000) in good yield details of which is given in example (Example I). The resulting 2,4,5-trimethoxyphenylpropane serve as a simple and economical starting material for generation of double bond in trans form (i.e. α-asarone) using dehydrogenating agents such as DDQ.

Introduction of double bond in a molecule is referred to as a dehydrogenation reaction, which can proceed, by the abstraction of either hydride ion (an ionic mechanism) or hydrogen atom or an electron (free radical mechanism). There are several known dehydrogenating reagents namely MnO2, DDQ, DCQ, Hg(OAc)$_2$, SeO$_2$,Pd/C, Se and S in which DDQ (2,3-dichloro-5,6-dicyano-1,4-benzoquinone) is found effective and facile dehydrogenating reagent for the conversion of 2,4,5-trimethoxyphenylpropane derivatives into trans-asarone. DDQ is widely used as a powerful dehydrogenating agent (Sondengam, B. L. and Kimbu, S. F., Tetrahedron Letters, 1, 69–70 (1977) and Guy, A.; Lemaire, M. and Guette, J. P., Chem. Commun., 8 (1980)) which acts as one electron oxidant (Becker, H. D., J. Org Chem. 30, 982 (1965). DDQ was first introduced for the dehydrogenation of tetralin and bibenzyl into naphthalene and stilbene respectively (Braude, E. A. and Waugh, T. D., J. Org. Chem., 30, 3240 (1965)). This high potential quinone has also found wide application (Walker, D. and Hiebert, J. D., Chem. Rev., 67, 153 (1967)), particularly in the field of steroids, and its scope has been extended for the dehydrogenation of ketones, alcohols and lactones etc. A number of allylic and benzylic alcohols react rapidly with DDQ at room temperature (Findlay, J. W. A. and Turner, A. B., J. Chem. Soc. (C), 23 (1971)), which undergo either coupling reactions or dehydrogenation, depending upon their structure. Rapid reaction with DDQ is also often observed in compounds containing activated tertiary hydrogen atoms (Brown, W. and Turner, A. B., J. Chem. Soc. (C), 2057 (1971)). In addition, the DDQ-mediated reactions allow to monitor the progress of the reaction as the green-coloured charge transfer (CT)-complex which is formed initially, starts changing into pink or brown colour (as the 2,3-dichloro-5,6-dicyano-1,4-hydrobenzoquinone crystallized out) and thus, indicates the formation of products. At the end of the reaction, the precipitated hydrobenzoquinone (DDQH$_2$) can be easily separated by filteration which allows to obtain 2,3-dichloro-5,6-dicyano-1,4-hydrobenzoquinone (DDQH$_2$) in 91 to 94% yield. The amount of precipitated hydroquinone (DDQH$_2$) is a convenient measure of the extent of hydrogen transfer. DDQH$_2$ so obtained can be conveniently converted back to DDQ in good yield by standard methods (Walker, D. and Waugh, T. D., J. Org. Chem., 30, 3240 (1965)). It is worthwhile to mention here that in view of all dehydrogenating reagents (such as chloranil, selenium dioxide, sulphur and selenium), DDQ is found to be effective dehydrogenating reagent towards formation of the carbon-carbon double bond, exclusively in trans form which has also been found in literature during conversion of 4,4'-dimethoxybibenzyl into trans-4,4'-dimethoxystilbene (Lemaira, M.; Guy, A. and Imbert, D., Chem. Commun., 741 (1986)) and Ireland, R. E. and Brown, G., Org. Synthesis, Coll. Vol.V, 428–431).

Interestingly, the interaction between DDQ and 2,4,5-trimethoxyphenylpropane largely depends upon time, temperature solvent and amount of reagent (DDQ). In polar anhydrous solvents namely alcohols such as methanol, ethanol, propanol and the like; ether such as tetrahydrofuran, dioxane and the like; chlorinated solvents such as dichloromethane, chloroform and the like, the reaction between 2,4,5-trimethoxyphenylpropane and varying amount of DDQ, preferably ranging from 1.0 to 1.1 moles, furnishes the corresponding dehydrogenated product i.e. α-asarone and unreacted starting material alongwith yellow coloured polar compound as a side product while 2,4,5-trimethoxyphenylpropane and varying amount of DDQ, preferably ranging from 1.1 to 1.3 moles in the same solvent, furnishes α-asarone as well as above yellow coloured compound but without any starting material (Example II). Addition of a catalytic amount of a solid support such as celite, silica gel, alumina, resin and the like dramatically accelerates the rate of dehydrogenation and increases the yield of α-asarone (Example III) as the concept of utilizing reagents adsorbed on inert supports for organic synthesis has also been recently employed by several chemists (Posner, G. H. and Rogers, D. Z., J. Am. Chem. Soc. 99, 8208 (1997); Jr. Filippo, J. S. and Chern, C. I., J. Org. Chem. 42, 2182 (1979)). Formation of side products are not surprising with oxidants like DDQ and many others such as PCC, MnO$_2$, KMnO$_4$, Cr(VI) etc. (Muzart, J. Tetrahedron Letters 28 (40) 4665–4668 (1987)). Initially, the side product (i.e. yellow band) was left several times inside the column (during column chromatography) considering it as unreacted DDQ since DDQ is itself a yellow coloured reagent, however, unsatisfactory yield of trans-asarone, induced us to separate each band and subsequently, to characterize them in details. Finally, the melting point of yellow solid (139–140° C.) ruled out the possibilities of DDQ (209–214° C.) and thereafter, we successfully characterized it as 2,4,5-trimethoxycinnamaldehyde on the basis of spectral data. The yellow solid showed IR absorption band at 1648 (conjugated C=O) cm$^{-1}$ and also gave a positive 2,4-DNP test, thus, confirming the presence of carbonyl group. The aldehydic nature of the carbonyl function was indicated by the Tollen's test. $^1$H NMR of yellow solid showed the 14 number of protons (Example II) which is less by two number of protons in comparison to Pasarone (Patra, A. and Mitra, A. K., Phytochemistry, 44, 668–669, (1981)) except for a doublet at δ 9.65 (1H, d, J=7.8 Hz) which could be assigned to an aldehyde proton coupled with an olefinic proton appearing as a doublet at δ 6.64 (1H, dd, J=15.8 Hz, J=7.8 Hz). This second proton formed a typical large coupling constant with the other olefinic proton δ 7.81 (1H, d, J=15.8 Hz) and also a kind of the large value of J is indicative of trans-stereochemistry. Further, the position of two aromatic singlet protons and three singlet for nine protons from trimethoxy groups are more or less at same δ value as starting material, however, appearance of three protons at δ 9.65 (1H, d), 7.81 (1H, d) and 6.64 (1H, dd,) finally supported the possibility of unsaturated aldehyde group (—CH═CH—CHO) attached to trimethoxy substituted phenyl ring. Similarly, the $^{13}$C NMR of the yellow solid (appeared at δ 194.1, 154.1, 153.2, 147.6, 143.3, 126.4, 114.5, 110.5, 96.5, 56.4, 56.2, 56.0)) clearly indicated the presence of 12 carbons which is similar to the 12 carbons of β-asarone except the position of side propyl group which appeared at δ 194.1 (C-3'), 154.1 (C-1') and 126.4 (C-2') is possible due to (—CH═CH—CHO) group. The EI mass spectrum of yellow solid showed a clear [M]$^+$ peak at m/z 222. This together with above $^1$H, $^{13}$C and IR data, the yellow solid was finally confirmed to be 2,4,5-trimethoxycinnamaldehyde as trans isomer which is later on discovered as naturally occurring rarer phenylpropanoid (Kulkami, M. M.; Sohoni, J.; Rojatkar, S. R. and Nagasampagi, B. A., Indian J Chem, 25B, 981 (1986)). It is also worthwhile to mention that the formation of trans-2,4,5-trimethoxycinnamaldehyde in a single step from phenylalkane i.e. 2,4,5-trimethoxypropanre opens new route for the synthesis of cinnamaldehyde derivatives and we have recently extended this finding towards development of a series of substituted cinnamaldehyde derivatives exclusively (Sinha, A. K., Joshi, B. P. and Dogra, R. U.S. patent applicaion Ser. No. 09/805,832 filed on Mar. 14, 2001 and Sinha, A. K., Joshi, B. P. and Dogra, R. PCT Patent No. IN 01/00104 filed on May 21, 2001), which is, in fact, a mild and simpler, than hitherto reported synthetic methods (U.S. Pat. No. 2,529,186, Nov. 7, 1950; Friedrich and Hartmann, Chem. Ber., 94, 838 (1961); Ger. Pat. 1,114,798, Oct. 12, 1961; U.S. Pat. No. 3,028,419, Apr. 3, 1962; Deuchert, S. K., Hertenstein, U. and Hunig, S., Synthesis, 777 (1973); El-Feraly, F. S. and Hoffstetter, M. D., J. Nat. Prod. 43, 407 (1980); Rajasekhar, D. and Subbaraju, G. V., Indian. J. Chem., 38, 837–838 (1999)). To the best of our knowledge, such two step hydrogenation of widely available allyl/ and/or propenyl phenyl into phenylpropane and then, dehydrogenation of phenylpropane into trans-phenylpropene derivative (α-asarone), has not been reported earlier, although alkaline isomerisation of allylphenyl always is well documented to provide trans-isomer but always with varying amount of toxic cis-isomer (β-asarone). Although above method provides α-asarone in 72% yield (Example II) but our main objective was still to increase the percentage of α-asarone and to subside or reduce the yield of abnormal formation of 2,4,5-trimethoxycinnamaldehyde during dehydrogenation/oxidation of 2,4,5-trimethoxyphenylpropane.

In order to further increase the yield of α-asarone, an alternative route appears to prepare intermediate 1-(2,4,5-trimethoxy)phenyl-1-propanone (isoacroramone) by treating 2,4,5-trimethoxyphenylpropane with DDQ in aqueous organic solvent which upon treatment with sodium borohydride into 1-(2,4,5-trimethoxyphenyl-1-hydroxypropane followed by acidic dehydration towards formation of α-asarone. The structure of 1-(2,4,5-trimethoxy)phenyl-1-propanone, a crystalline solid (mp 109–110° C.), was confirmed on the basis of spectral data (Example IV) which is later on discovered as a naturally occurring rarer phenylpropanoid, isolated from *Acorus tatarinowii* as a light yellowish viscous gum, however, our method afforded isoacoramone as a crystalline solid with the similar spectral data as natural isoacoramone (Jinfeng, Hu and Xiaozhang, Feng, Planta Medica, 66, 662–664 (2000)). It is also worthwhile to mention that the formation of 1-(2,4,5-trimethoxyphenyl)-1-propanone in a single step from phenylalkane i.e. 2,4,5-trimethoxypropane opens new route for the synthesis of phenylpropanone derivatives which is, in fact, a mild, simple and free from drawbacks generally exist with reported synthetic methods and some of reported methods are:

(a) Friedel Craft reaction of aryl or substituted aryl group with AlCl$_3$ and acyl chloride into aryl ketone, however, methoxy substituted aryl may lead to some degree of demethoxylation with AlCl$_3$ during Friedel Craft reaction (Horie, T., Tominaga, H., Kawamura, Y., Hada, T., Ueda, N., Amano, Y. and Yamamoto, S., J. Med. Chem., 34, 2169–2176 (1991) and Shaun, R. S.; Christopher, J. C.; Rosanna, T.; Gisele, N.; Kathryn, C.; Jun, S.; Benita, S. K. and J, A. K., J. Med. Chem., 43, 4934–4947 (2000)).

(b) preparation by the acylation of substituted benzene derivatives using acid catalyst such as TiCl$_4$, FeCl$_3$, SnCl$_4$, CF$_3$SO$_3$H, Nafion-H and metal oxides etc. (Brown, H. C. and Marino, G., J. Am. Chem. Soc., 81, 3308 (1959); Olah, G. A.; Malhotra, R.; Narang, S. C. and Olah, J. A., Synthesis, 672 (1978) and Yamaguchi, T., Appl. Catal., 61,1 (1990)).

(c) preparation by oxidation of benzylic hydrocarbon to ketone with calcined ZnCrCO$_3$, NiAlCO$_3$, CuZnAlCO$_3$ and MgAlCO$_3$ (hydrotalcite) (Choudhary, B. M.; Bhuma, V. and Narender, N., Indian J. Chem, 36B, 278–280 (1997)).

(d) preparation in several steps by reaction of vanillin acetate with propyl iodide/Mg ribbon followed by dehydrogenation of carbinol derivative into phenylpropanone (Suri, O. P., Bindra, R. S., Satti, N. K. and Khajuria, R. K., Indian J. Chemistry, 26B, 587–588 (1987)).

(e) preparation by phenyllithium compounds and Grignards reagents with lithium carboxylates (Levine, R.; Karten, M. J. and Kaudunce W. M., J. Org. Chem., 40, 1770–1773 (1975)).

(f) preparation by reaction of propionic acid and iron (II) salt with benzoic acid (Granito, C. and Schultz, H. P., J. Org. Chem., 879–881 (1963)).

(g) preparation by reaction of methoxylated benzene with propyl chloride using zeolite H-beta catalysts (Jaimol, T.; Moreau, P.; Finiels, A.; Ramaswamy, A. V. and Singh, A. P., Applied Catalysis A: General, 214, 1–10 (2001)).

It is also worthwhile to mention that 1-(2,4,5-trimethoxy)phenyl-1-propanone (also known as 2,4,5-trimethoxypropiophenone) has been isolated, so far, from well known two medicinal plants (*Acorus tatarinowii* and *Piper marginatum*), but, only in trace amounts. Thus, preparation of 2,4,5-trimethoxypropiophenone (isoacoramone) in sufficient quantity has not only allowed to facilitate its more rigorous biological evaluation known for structurally similar propiophenone derivatives (Kuchar, M.; Brunova, B.; Rejholec, V.; Roubal, Z. and Nemecek, O., Collection Czechoslov. Chem., 41, 633–646 (1976); Lariucci, C.; Homar, L. I. B.; Ferri, P. H. and Santos, L. S., Anais Assoc. Bras. Quim., 44(3), 22–27 (1995); Stauffer, S. R.; Coletta, C. J.; Tedesco, R.; Nishiguchi, G.; Carlson, K.; Sun, J.; Katzenellenbogen, B. S. and Katzenellenbogen, J. A., J. Med. Chem., 43, 4934–4947 (2000) and Jaimol, T.; Moreau, P.; Finiels, A.; Ramaswamy, A. V. and Singh, A. P., Applied Catalysis A: General, 214, 1–10 (2001)) but also as a synthon for the preparation of α-asarone via reduction of 2,4,5-trimethoxypropiophenone with sodium borohydride and the like into 1(2,4,5-trimethoxyphenyl)-1-hydroxypropane followed by its acidic dehydration with p-toluene sulphonic acid) (Example VI and VII).

All the methods reported so far for the synthesis of α-asarone (Francisco, D.; Leticia, C.; Rosa, F.; Joaquin, T.; Fernando, L.; German, C.; Heber, M. Org. Prep. Proced. Int. 23 (2), 133–138 (1991); Wang, Z.; Jiang, L. and Xingxiang, X., Youji Huaxue, 10 (4), 350–352 (1990); Shirokova, E. A.; Segal, G. M. and Torgov, I. V., Bioorg. Khim., 11 (2), 270–275 (1985) and Janusz, P.; Bozena, L.; Alina, T. D.; Barbara, L.; Stanislaw, W.; Danuta, S.; Jacek, P.; Roman, K.; Jacek, C.; Malgorzata, S. and Zdzislaw, C., J. Med. Chem., 43, 3671–3676 (2000)); Nenokichi, H. and Shibamoto, N., Kinki Daigaku Rikogakubu Kenkyu Hokoku, 12, 63–66 (1977); Saxena, D. B. and Mukeijee, S. K., Indian J. of Chem., 24B, 683–684 (1985)) have various limitations and none of them have been found suitable for the economical production of α-asarone. In seeking a simple synthesis of α-asarone from a cheaper material and reagents, 2,4,5-trimethoxyphenylpropane (isolated from hydrogenation of commercially available *Acorus calamus* oil rich in asarones content) appears as a simple and economical starting material in which 2,4,5-trimethoxyphenylpropane undergoes dehydrogenation and oxidation to afford not only α-asarone but also rarer phenylpropanoids of biological importance namely isoacoramone and 2,4,5-trimethoxycinnamaldehyde. In the present invention, the formation of cc-asarone is the first example of DDQ assisted one step synthesis of α-asarone from toxic β-asarone via 2,4,5-trimethoxyphenylpropane which, in fact, would offer the advantages of simplicity and directness and can be applied for large scale preparations.

EXAMPLES

The invention will now be described by way of example with refrence to the accompanying examples which are provided for the purpose of illustration and are not to be constructed as being limiting on the present invention.

Example 1

Preparation 2,4,5-trimethoxyphenylpropane (dihydro asarone): The starting material 2,4,5-trimethoxyphenylpropane is prepared by hydrogenation of β-asarone (isolated from *Acorus calamus* oil) or of commercially available *calamus* oil rich in asarones (i.e. β and/or α,γ-asarone) content.

(a) Hydrogenation of β-asarone into 2,4,5-trimethoxyphenylpropane (dihydro asarone):

β-asarone was isolated by loading the crude *calamus* oil (17.00 g) on silica gel column and then eluted the column with hexane to remove unwanted non-polar compounds. Subsequent elution with hexane-ethylacetate mixture with increasing proportion of ethylacetate upto 10% gave 13.94 g (82%, w/w) of pure liquid; $R_f$ 0.63 (hexane:toluene:ethylacetate=1:1:0.1); $^1H$ NMR (CDCl$_3$, 300 MHz) δ 6.84 (1H, s, H-6), 6.53 g(1H, s, H-3), 6.50 (1H, dd, J=15.8 Hz and 1.5 Hz, H-1'), 5.78 (1H, dq, J=6.5 Hz and 15.8 Hz, H-2'), 3.88, 3.83 and 3.79 (s, 3H, each, 3-OCH$_3$) and 1.85 (3H, dd, J=6.5 Hz and 1.5 Hz, H-3'); $^{13}C$ NMR (CDC$_3$, 75.4 MHz) δ 151.4 (C-2), 148.5 (C-4), 142.3 (C-5), 125.5 (C-1'), 124.7 (C-2'), 118.0 (C-1), 114.1 (C-6), 97.6 (C-3), 56.5 , 56.2 & 55.9 (3× OCH$_3$) and 14.5 (C-3'); EIMS m/z 208 (M$^+$, 100), 193 (M$^+$–Me, 46), 165 (M$^+$–C$_3$H$_7$, 24). On the basis of above spectral data and comparing with reported literature (Gonzalez, M. C.; Sentandrew, M. A.; Rao, K. S.; Zafra, M. C. and Cortes, D., Phytochemistry 43,1361–1364 (1996)), the liquid was identified as β-asarone in 94% purity (by GC, performed on a Shimadzu-GC-14B gas chromatograph with the following conditions: SE-30 column; 30 m×0.25 mm; injector 250°/C.; FID detector 230°/c.; temp. programme 40 (hold for 2 min.) to 220° C. (hold for 10 min.), 10° c. min$^{-1}$; vol. 1 μl; N$_2$ flow 30 ml/min; H$_2$ flow 40 ml/min.; airflow 300 ml/min.; split injection ratio 1:30)

The β-asarone (6.00 g, 0.029 mol) in 160 ml of ethanol is stirred with 10% palladium on activated charcoal (0.80 g) and ammonium formate (17.00 g, 0.27 mol) at room temperature under nitrogen atmosphere till the disappearance of starting material. The catalyst was removed by filtration and the solvent was evaporated under reduced pressure. The residue was partitioned between ethyl acetate and water and the ethyl acetate layer washed with water, dried (Na$_2$SO$_4$) and filtered. Evaporation of filtrate left a liquid, which was chromatographed, on silica gel using hexane-ethyl acetate mixture with increasing proportion of ethyl acetate upto 10% as the eluent. The eluate was evaporated to give 5.87 g (97%) of a clear sweet and pleasant liquid; $R_f$ 0.69 on silica gel plate (hexane:toluene:ethylacetate=1:1:0.1) which solidified below 0° C.; $^1H$ NMR (DMSO-d6) δ 6.72 (1H, s, H-6), 6.62 (1H, s, H-3), 3.76 to 3.68 (9H, s, 3-OCH$_3$), 2.5 (2H, t, C-1'), 1.6 (2H, m, C-2') and 0.9 (3H, t, C-3'); $^{13}C$ NMR (CDCl$_3$) δ 151.4 (C-2), 147.4 (C-4), 142.7 (C-5), 122.7 (C-1), 114.3 (C-6), 98.0 (C-3) and 56.5, 56.2 & 56.0 (3x OCH$_3$), 31.6 (C-1'), 23.3 (C-2') and 13.79 (C-3'); EIMS m/z 210 (M$^+$, 39), 181(M$^+$–C$_2$H$_5$, 100), 167 (M$^+$–C$_3$H$_7$, 5), 151 (M$^+$–OCH$_3$+CO, 29), 136 (M$^+$–C$_3$H$_7$+OCH$_3$, 10). On the basis of $^1H$ NMR, $^{13}C$ NMR and Mass spectral data, the above liquid was identified as 2,4,5-trimethoxyphenylpropane in 99% purity (by GC).

(b) Hydrogenation of crude *Acorus calamus* oil into dihydro asarone: In this method 42.00 g of crude calamus oil (rich in β and/or α,γ-asarone) in 300 ml methanol was hydrogenated in the paar reactor with 10% Pd/C (4.80 g) at 10–40 psi at room temperature till the disappearance of starting material. The catalyst was filtered and the solvent was removed under reduced pressure, which afforded 39.9 g (95 w/w) of reduced oil. Column purification of reduced oil on silica gel column using above eluent system (hexane-ethyl acetate mixture) gave 2,4,5-trimethoxyphenylpropane (35.76 g) as a liquid in 85% yield (w/w); $R_f$ 0.69 (hexane:toluene:ethylacetate=1:1:0.1); $^1H$ NMR (CDCl$_3$) of liquid appeared at δ 6.81 (1H, s, H-6), 6.32 (1H, s, H-3), 3.84 to 3.78 (9H, s, 3-OCH$_3$), 2.4 (2H, t, C-1'), 1.6 (2H, m, C-2'), 0.9 (3H, t, C-3'). On the basis of spectral data, the liquid was identified as 2,4,5-trimethoxyphenylpropane.

Example II

Preparation of α-asarone (trans-2,4,5-Trimethoxyphenylpropene) via dehydrogenation of 2,4,5-trimethoxyphenylpropane with DDQ: A solution of DDQ (2.04–2.65 g) in anhydrous dioxane (40 mL) was added dropwise over a period of 10–15 min to a ice cold and well stirred solution of 2,4,5-trimethoxyphenylpropane (1.89 g, 0.009 mol) in anhydrous dioxane (55 mL) and stirring was continued at room temperature for over night under inert atmosphere. The precipitated solid (DDQH$_2$) was filtetred and further washed twice with dioxane. The combined dioxane was evaporated and concentrate was poured into water and then extracted with dichloromethane (3×70 mL). The combined organic layers were washed with brine (3×15 mL), 10% sodium bicarbonate (2×10 mL), brine (3×15 mL) and dried over anhydrous sodium sulphate. The residue obtained on evaporation of the solvents was chromatographed on silica gel column using hexane-ethyl acetate mixture with increasing proportion of ethyl acetate upto 40% and the fractions having similar $R_f$ were mixed which after evaporation of the solvents provided two viscous liquids which were further crystallized from mixture of hexane and methanol to afford 0.90 g of a white solid (48%, mp 44–45° C.) and 0.18 g of a yellow solid (9%, mp 139–140° C.) as a side product.

White solid (mp 44–45° C.) as obtained above has $R_f$ 0.63 (hexane:toluene:ethylacetate:: 1:1:0.1); $^1$H NMR (CDCl$_3$): δ 6.91 (1H, s, H-6), 6.64 (1H, dd, J=1.5 Hz and 16 Hz, H-1'), 6.45 (1H, s, H-3), 6.02 (1H, dq, J=6.2 Hz and 16.0 Hz, H-2'), 3.84, 3.81 and 3.77 (each 3H, s, three OCH$_3$), 1.87 (3H, dd, J=6.2 Hz and 1.5 Hz, H-3'); $^{13}$C NMR (CDCl$_3$): δ 149.9 (C-2), 148.0 (C-4), 142.6 (C-5), 124.4 (C-1'), 123.4 (C-2'), 118.3 (C-1), 109.2 (C-6), 97.3 (C-3), 56.1, 55.7 & 55.1 (3-OCH$_3$), 18.7 (C-3'); EIMS m/z 208 (M$^+$, 100), 193 (74), 177 (24), 165 (26), 137 (12), 105 (8), 91 (26), 77 (24), 69 (34), 65 (8), 53 (16). On the basis of above spectral data and comparing with reported literature (Patra, A. and Mitra, A. K., J. Nat. Prod. 44, 668–669 (1981) and Gonzalez, M. C.; Sentandrew, M. A.; Rao, K. S.; Zafra, M. C. and Cortes, D., Phytochemistry 43:1361–1364 (1996)), the white solid (mp 44–45° C.) was identified as aα-asarone.

Yellow solid (mp 139–140° C.) obtained as side product was identified as trans-2,4,5-trimethoxycinnamaldehyde having $R_f$=0.45 (hexane-ethyl acetate; 4:1); $^1$H NMR δ 9.65 (1H, d, J=7.8 Hz, H-3'), 7.81 (1H, d, J=15.8 Hz, H-1'), 7.03 (1H, s, H-6), 6.64 (1H, dd, J=15.8 Hz, J=7.8 Hz, H-2'), 6.51 (1H, s, H-3), 3.95. 3.91 and 3.87 (each 3H, s, three OCH$_3$); $^{13}$C NMR δ 194.1 (C-3'), 154.1 (C-1'), 153.2 (C-2), 147.6 (C-4), 143.3 (C-5), 126.4 (C-2'), 114.5 (C-1), 110.5 (C-6), 96.5 (C-3), 56.4 (5-OCH$_3$), 56.2 (2-OCH$_3$), 56.0 (4-OCH$_3$); EIMS m/z 222 [M]$^+$ (44), 207 (18), 191 (100), 179 (14), 171 (27), 151 (14), 147 (7), 69 (58), 58 (80); IR (film) νmax 1648 (conjugated carbonyl), 1602, 1504, 1466, 1448, 1350, 1254, 1120, 1024, 856 cm$^{-1}$; UV (MeOH) λmax 244, 298, 366 nm. On the basis of above spectral data and comparing with reported literature, the yellow solid (mp 139–140° C.) was identified trans-2,4,5-trimethoxycinnamaldehyde.

Example III

Preparation of α-asarone via dehydrogenation of 2,4,5-trimethoxyphenylpropane with DDQ containing little amount of silica gel: Addition of a catalytic amount of silica gel (0.2–0.6 g) drastically accelerated the rate of reaction as well as improved the yield of α-asarone when above dehydrogenation process (Example II-a) was conducted under the same condition resulting α-asarone in 72% yield and trans-2,4,5-trimethoxycinnamaldehyde in 18% yield.

Example IV

Preparation of Isoacoramone (1-(2,4,5-trimethoxyphenyl)-1-propanone): A solution of DDQ (3.06–4.09 g) in dioxane (40 mL) was added dropwise over a period of 10 min to a ice cold and well stirred solution of 2,4,5-trimethoxyphenylpropane (1.89 g, 0.009 mol) in wet dioxane or ethanol (55 mL) and the resulting mixture was stirred at room temperature for over night. The precipitate was filtered and further washed twice with dioxane. The combined dioxane layer was evaporated and mixture was poured into water and extracted with dichloromethane (3×70 mL). The combined organic layer were washed with brine (3×15 mL) and dried over sodium sulphate. The residue obtained on evaporation of the solvents was chromatographed on silica gel column using hexane-ethyl acetate mixture with increasing proportion of ethyl acetate upto 40% to afford viscous liquid which was crystallized from ethylacetate/hexane to afford 1.19 g (59%) of white crystals of isoacoramone. The spectral data was found similar as mentioned above in Example III.

Example V

Preparation of 1-(2,4,5-trimethoxyphenyl)-1-propanol: A solution of the isoacoramone (1.12 g, 0.005 mol) in 40 mL of THF was stirred at below −5° C. A pre-cooled solution of NaBH$_4$ (0.24–0.39 g) in water (1.2–1.8 mL) was added dropwise while maintaining the temperature of the reaction mixture below 0° C. After complete addition of NaBH$_4$, few drop of 10% NaOH was added and the reaction mixture was left overnight for stirring at room temperature. Finally, the reaction mixture was diluted with saturated ammonium chloride solution (20 mL) and kept stirring at room temperature for 20 min. THF was removed under reduced pressure and the mixture extracted twice with EtOAc. The EtOAc solution was washed twice with H$_2$O (twice), twice with brine, and then filtered. The filtrate was dried over sodium sulphate and evaporated to dryness. The residue obtained on evaporation was found enough pure for next step, however, it was chromatographed on neutral alumina column using using hexane-ethyl acetate mixture with increasing proportion of ethyl acetate upto 25% to afford 1-(2,4,5-trimethoxy)phenyl-1-propanol (1.01 g, 89%) as a liquid which after crystallization gave white solid; $R_f$ 0.78 (28% ethylacetate in hexane); mp 98–99° C.; $^1$H NMR (CDCl$_3$) at δ 7.06 (1H, s, H-6), 6.50 (1H, s, H-3), 4.45 (1H, t, J=6.6 Hz, H-1'), 3.91, 3.89 and 3.68 (each 3H, s, three —OCH$_3$), 1.81–1.54 (2H, m, H-2'), 0.85 (3H, J=7.4 Hz, H-3'); $^{13}$C NMR (CDCl$_3$) δ 152.0 (C-2), 148.5 (C-4), 143.7 (C-5), 123.77 (C-1), 110.9 (C-6), 97.9 (C-3), 73.4 (C-1'), 57.0 (4-OCH$_3$), 56.7 (5-OCH$_3$), 56.43 (2-OCH$_3$), 31.9 (C-2'), 11.0 (C-3'); IR (KBr) 3300 cm-1 (OH).

Example VI

Preparation of α-asarone (trans-2,4,5-trimethoxyphenyl-1-propene): The catalytic amount of p-toluene sulphonic acid (0.4–0.6 g) was added to a solution of 1-(2,4,5-trimethoxy)phenyl-1-propanol (0.90 g, 0.004 mol) in toluene (80 mL). The mixture was allowed to reflux for 12–14 hr under Dean Stark apparatus. Finally, the mixture was poured into an ice cold water and extracted with toluene (3×70 mL). The combined organic layer were washed with brine (3×15 mL), saturated sodium bicarbonate (2×10 mL), brine (3×15 mL), and dried over sodium sulphate. The residue obtained on evaporation of the solvents was chromatographed on silica gel column using hexane-ethyl acetate mixture with increasing proportion of ethyl acetate upto 10% to afford pure α-asarone (0.72 g, 87%) as a white solid having mp 44–45° C. The spectral data was found as same as mentioned above (Example II).

The main advantages of the present invention are:
1. A process discloses DDQ as a versatile reagent to provide a wide range of rarer phenylpropanoids namely .α-asarone, 2,4,5-trimethoxtcinnamaldehyde and 1-(2,4,5-trimethoxy)phenyl-1-propanone (isoacoramone) in one step with varying solvents, time, temperature and amount of dehydrogenating DDQ reagent.
2. A simple process for the preparation of pharmacologically active .α-asarone from 2,4,5-trimethoxyphenylpropane which is, in fact, the hydrogenated product of toxic β-asarone isolated from commercially available *calamus* oil.

3. A simple process for utilization of internationally banned but widely available toxic β-asarone rich *calamus* oil via two steps process i.e. hydrogenation and dehydrogenation into well known pharmacologically active α-asarone, thereby, enhancing the profitable use of *Acorus calamus* of tetraploid or hexaploid varieties (distributed extensively in Asian countries).

4. A simple process for the preparation of α-asarone exclusively without any contamination of corresponding isomeric forms of asarone (i.e. β and/or γ-isomer).

5. A process for the preparation of a non or less toxic compound (i.e. α-asarone) from toxic compound (i.e. β-asarone).

6. The process enables us to convert mixture of all the three isomeric forms of phenylpropenes (i.e. α,β and γ-asarone) firstly into 2,4,5-trimethoxyphenylpropane (via hydrogenation) and then regenerating phenylpropene (via. dehydrogenation) but exclusively in trans form (i.e. α-asarone) whereas previously reported method always provide α-asarone with varying amount of toxic β-asarone, during alkaline isomerization of γ-asarone and the like.

7. A process to prepare α-asarone from 2,4,5-trimethoxyphenylpropane using mild dehydrogenating DDQ reagent for the first time.

8. A process for the preparation of naturally occurring rare trans-2,4,5-trimethoxycinnamaldehyde in a single step from phenylpropane derivative which, in fact, discovered during preparation of α-asarone from 2,4,5-trimethoxyphenylpropane.

9. A process provides alternative route for the preparation α-asarone starting from 2,4,5-trimethoxypropiophenone obtained by treating 2,4,5-trimethoxyphenylpropane with DDQ in aqueous solvent.

10. A process provides 2,4,5-trimethoxypropiophenone as solid whereas natural 2,4,5-trimethoxypropiophenone (isolated from *Acorus tatarinowii* and *Piper marginatum*) is reported as viscous gum.

12. A process wherein formation of 2,4,5-trimethoxypropiophenone opens a new synthetic route for the preparation of a series of propiophenone derivatives in single step from phenylpropane derivatives i.e. 2,4,5-trimethoxyphenylpropane.

14. A process forms naturally occurring 2,4,5-trimethoxypropiophenone in sufficient quantity provides the opportunity for the its wide range of biological evaluation.

15. A process provides α-asarone exclusively via reduction of 2,4,5-trimethoxypropiophenone into 2,4,5-trimethoxyphenyl-1-hydroxypropane in high yield followed by acidic dehydration using p-toluenesulphonic acid and thionyl chloride/pyridine and the like.

What is claimed is:

1. A process for the preparation of pharmacologically active α-asarone (trans isomer) of formula II from toxic β-asarone (cis isomer) or β-asarone rich *Acorus calamus* oil containing α and γ-isomer, the said process comprises steps of:

(a) hydrogenating β-asarone or β-asarone rich *calamus* oil containing α and γ-asarone using 10% Pd/C catalyst, with or without ammonium formate under a pressure of 0–40 psi at room temperature, (b) purifying the product of step (a) over silica gel by performing column chromatography to obtain compound of formula (I),

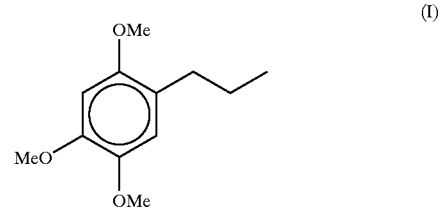

(c) dehydrogenating under inert atmosphere of compound of formula (I) of step (b) by treating with DDQ containing optionally silica or alumina in anhydrous organic solvent at room temperature for a period of 0.5 to 72 hours, (d) filtering the reaction mixture of step (c) to remove precipitated (DDQH$_2$) washing the residue with an organic solvent and obtaining combined clear filtrate, (e) concentrating the combined filtrate of step (d) and pouring the concentrate into water, extracting with water immiscible organic solvent, (f) combining organic solvent extract of step (e), washing with brine, 10% aqueous bicarbonate, followed again by brine, drying over anhydrous sodium sulphate, filtering and evaporating to dryness to obtain a residue, (g) purifying the residue of step (f) over silica gel column, eluting with mixture hexane:ethylacetate to obtain α-asarone as a viscous liquid and an yellow solid characterised as trans-2,4,5-trimethoxy cinnamaldehyde of formula (IIa),

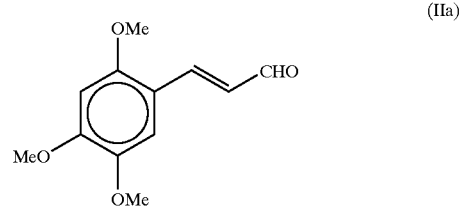

(h) crystallising the viscous liquid containing α-asarone using hexane:methanol mixture to afford white solid of α-asarone, (II)

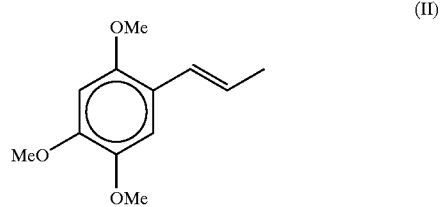

(i) obtaining α-asarone also from compound of formula (I) of step (a) by treating with DDQ in an aqueous organic solvent at room temperature for a period of 16–20 hours, (j) filtering the reaction mixture of step (i) to remove precipitated solid (DDQH$_2$), washing the residue with an organic solvent and obtaining a clear solution, (k) evaporating the clear solution of step (j) and pouring the residue into water, extracting with organic solvent washing the organic solvent extract with brine, drying over anhydrous sodium sulphate, filtering and evaporating to obtain a residue, (l) purifying the residue of step (k) over silica gel column, eluting with mixture of hexane:ethyl acetate to obtain a viscous liquid fraction containing isoacoramone which is crystallised from ethylacetate:hexane to afford white crystals of isoacoramone of formula (III),

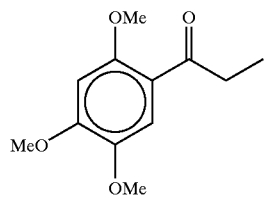

(III)

(m) treating compound of formula (III) of step (l) with sodium borohydride in an organic solvent in presence of aqueous alkali hydroxide solution at a temperature range of −5° C. to room temperature for a period of 16–20 hours, (n) diluting the reaction mixture of step (m) with saturated ammonium chloride solution, stirring for 20–30 minutes, (o) removing the organic solvent from solution of step (n) under reduced pressure and extracting the aqueous layer with ethyl acetate, (p) washing the ethyl acetate layer of step (o) with water, drying ethyl acetate layer over anhydrous sodium sulphate, filtering and evaporating the organic solvent to dryness to obtain a residue, (q) purifying residue of step (p) over neutral alumina column using an eluant hexane:ethylacetate to afford 1-(2,4,5-trimethoxy)-phenyl-1-propanol of formula (IIIa),

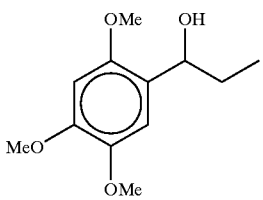

(IIIa)

(r) dehydrating the compound of formula (IIIa) by treating with p-toluene sulphonic acid in an aromatic hydrocarbon solvent at a reflux temperature using Dean-stack apparatus for continuous removal of water, (s) pouring the reaction mixture of step (r) into cold water, extracting with aromatic hydrocarbon solvent and separating organic layer, (t) washing the organic layer of step (s) with brine, saturated bicarbonate solution again followed by brine, drying over anhydrous sodium sulphate, filtering and evaporating organic solvent to obtain a residue, and (u) purifying the residue of step (t) over silica gel column, eluting with hexane:ethyl acetate mixture to obtain a white solid α-asarone of formula (II).

2. A process as claimed in claim 1 wherein in steps (c) and (d) the anhydrous organic solvent used is selected from a group consisting of methanol, ethanol hexane, benzene, toluene, tetrahydrofuran and dioxane.

3. A process as claimed in claim 1 wherein in step (c) the molar ratio of DDQ to 2,4,5-trimethoxy phenylpropane used is in the range of 1:1 to 1.3:1.

4. A process as claimed in claim 1 wherein in step (i) the molar ratio of DDQ to 2,4,5-trimethoxy propane of Formula (I) used is in the range of 1.6:1 to 2.1:1.

5. A process as claimed in claim 1 wherein dehydrogenation of 2,4,5-trimethoxy propane of formula (I) provides α-asarone of the Formula (II) with 51% yield and an yellow solid 2,4,5-trimethoxy cinnamaldehyde of formula (II) with 11% yield.

6. A process as claimed in claim 1 wherein in step (c) the addition of catalytic amount of silica gel or alumina enhances the yield of α-asarone up to 72% and trans2,4,5-trimethoxy benzaldehyde upto 18%.

7. A process as claimed in claim 1 wherein in step (e), the water immiscible organic solvent used is selected from carbon tetrachloride, dichloromethane and chloroform.

8. A process as claimed in claim 1 wherein in steps (i) and (j) the organic solvent used is selected from a group consisting of methanol, ethanol, hexane, benzene, toluene, tetrahydrofuran and dioxane.

9. A process as claimed in claim 1 wherein in step (i) the ratio of water:organic solvent used is in the range of 0.1:9.9 to 1:9.

10. A process as claimed in claim 1 wherein in step (k) the organic solvent used is selected from a group consisting of methanol, ethanol, tetrahydrofuran and dioxane.

11. A process as claimed in claim 1 wherein in step (m) the organic solvent used is tetrahydrofuran.

12. A process as claimed in claim 1 wherein in step (r) dehydrating agent used is either p-toluene sulphonic acid or thionylchloride pyridine.

13. A process as claimed in claim 1 wherein in step (r) the aromatic hydrocarbon solvent used is selected from the group consisting of benzene, toluene and xylene.

14. A process as claimed in claim 1 wherein in step (u) the yield of α-asarone is up to 87%.

15. A process as claimed in claim 1 is preferably carried out at a temperature in the range of 20°–70° C. for a period of 4–12 hours.

16. A process as claimed in claim 1 wherein in step (l) the isoacoramone (2,4,5-trimethoxy propiophenone) of formula (III) is obtained as a crystalline solid having m.p. 107–110° C.

17. A process as claimed in claim 1 which yields α-asarone in high purity, which is completely devoid of β and γ-asarone.

18. A process as claimed in claim 1, wherein in steps (c) and (d) the anhydrous organic solvent used is anhydrous dioxane.

19. A process as claimed in claim 1, wherein in step (e), the water immiscible organic solvent used is dichloromethane.

20. A process as claimed in claim 1, wherein in steps (i) and (j) the organic solvent used is either ethanol or tetrahydrofuran.

21. A process as claimed in claim 1, wherein in step (k) the organic solvent used is either ethanol or dioxane.

22. A process as claimed in claim 1, wherein in step (r) the aromatic hydrocarbon solvent used is toluene.

* * * * *